US012661414B2

(12) United States Patent
Exner et al.

(10) Patent No.: US 12,661,414 B2
(45) Date of Patent: Jun. 23, 2026

(54) STABILIZED NANOBUBBLES AND MICROBUBBLES FOR DIAGNOSTIC AND THERAPEUTIC APPLICATIONS

(71) Applicants: CASE WESTERN RESERVE UNIVERSITY, Cleveland, OH (US); University Hospitals Cleveland Medical Center, Cleveland, OH (US)

(72) Inventors: Agata Exner, Shaker Heights, OH (US); Al de Leon, Cleveland, OH (US); Reshani Perera, Twinsburg, OH (US); Pinunta Nittayacharn, Cleveland, OH (US)

(73) Assignees: CASE WESTERN RESERVE UNIVERSITY, Cleveland, OH (US); UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 0 days.

(21) Appl. No.: 17/043,531

(22) PCT Filed: Mar. 29, 2019

(86) PCT No.: PCT/US2019/024782
§ 371 (c)(1),
(2) Date: Sep. 29, 2020

(87) PCT Pub. No.: WO2019/191557
PCT Pub. Date: Oct. 3, 2019

(65) Prior Publication Data
US 2021/0106699 A1 Apr. 15, 2021

Related U.S. Application Data

(60) Provisional application No. 62/650,178, filed on Mar. 29, 2018.

(51) Int. Cl.
*A61K 49/22* (2006.01)
*A61K 9/51* (2006.01)

(52) U.S. Cl.
CPC .......... *A61K 49/223* (2013.01); *A61K 9/5123* (2013.01)

(58) Field of Classification Search
CPC .... A61K 49/223; A61K 9/0009; A61K 47/24; A61K 41/0028; A61K 9/5123; A61K 9/0019
See application file for complete search history.

(56) References Cited

U.S. PATENT DOCUMENTS

| | | | | |
|---|---|---|---|---|
| 5,923,304 A * | 7/1999 | Edwards | H01Q 21/29 | 343/893 |
| 6,051,207 A * | 4/2000 | Klaveness | A61K 51/0497 | 424/9.1 |
| 6,217,850 B1 * | 4/2001 | Dugstad | A61K 49/227 | 427/213.3 |
| 6,416,740 B1 | 7/2002 | Unger | | |
| 9,687,570 B2 * | 6/2017 | Wang | A61K 41/0028 | |
| 9,801,959 B2 | 10/2017 | Unger et al. | | |
| 2007/0269381 A1 * | 11/2007 | Walovitch | A61K 49/223 | 424/9.52 |
| 2008/0200862 A1 * | 8/2008 | Unger | A61K 47/6901 | 604/518 |
| 2014/0147390 A1 * | 5/2014 | Exner | A61K 9/1271 | 424/9.52 |
| 2015/0023881 A1 * | 1/2015 | Kim | A61K 49/223 | 424/9.52 |
| 2016/0030596 A1 | 2/2016 | Kheir et al. | | |
| 2018/0036437 A1 * | 2/2018 | Holland | A61K 33/00 | |
| 2018/0064831 A1 | 3/2018 | Basilion et al. | | |

FOREIGN PATENT DOCUMENTS

| | | |
|---|---|---|
| WO | 199428780 A2 | 12/1994 |
| WO | 199524184 A1 | 9/1995 |
| WO | 2017210612 A1 | 12/2017 |

OTHER PUBLICATIONS

Fan et al., Nanotechnology, 2013, 24, 325102 (10pp). (Year: 2013).*
Wang et al., PLOS One, 2014, 9(5), e96586 (12pp)). (Year: 2014).*
Bodera et al., 2018 IEEE International Ultrasonics Symposium (IUS), Kobe, Japan, 2018, pp. 1-4. (Year: 2018).*
Nittayacharn et al., 2018 IEEE International Ultrasonics Symposium (IUS), Kobe, Japan, 2018, pp. 1-4. (Year: 2018).*
Liu et al., Biomaterials, Apr. 2018, 162, p. 200-207. (Year: 2018).*
Krupka et al., Mol Pharm. 2010; 7:49-59 (Year: 2010).*
Applicant: Case Western Reserve University; "Stabilized Nanobubbles and Microbubbles for Diagnostic and Therapeutic Applications" International Application No. PCT/US2019/024782; International Filing Date: 22019-03-29; PCT International Search Report and Written Opinion; Authorized Officer: Lee W. Young; Date of Completion: May 28, 2019; 8 pgs.
Applicant: Case Western Reserve University; "Stabilized Cross-linked Nanobibbles for Diagnostic and Therapeutic Application" U.S. Appl. No. 16/306,840, filed Dec. 3, 2018; Office Action dated May 26, 2022; 21 pgs.

(Continued)

*Primary Examiner* — Michael G. Hartley
*Assistant Examiner* — Leah H Schlientz
(74) *Attorney, Agent, or Firm* — Tarolli, Sundheim, Covell & Tummino LLP

(57) ABSTRACT

A composition includes a plurality of stabilized nanobubbles and/or microbubbles. Each nanobubble and/or microbubble has a lipid membrane that defines at least one internal void, which includes at least one gas, the membrane including a plurality of lipids, an edge-activator, which is incorporated between lipids of the membrane and enhances the flexibility of the nanobubbles and/or microbubbles, and a membrane stiffener, which is incorporated on an outer surface of the membrane and enhances the membranes resistance to tearing.

11 Claims, 33 Drawing Sheets

(56) References Cited

OTHER PUBLICATIONS

Sheng Yingjie, et al.; "Magnetically responsive microbubbles as delivery vehicles for targeted sonodynamic and antimetabolite therapy of pancreatic cancer"; Journal of Controlled Release, vol. 262, Sep. 1, 2017; pp. 192-200, XP055867600, Amsterdam, NL; ISSN: 0168-3659, DOI: 10.1016/j.jconrel.2017.07.040.

Liu Jinfeng, et al.; "Ultrasound molecular imaging of acute cardiac transplantation rejection using nanobubbles targeted to T lymphocytes", Biomaterials, Elsevier, Amsterdam, NL, vol. 162, Feb. 8, 2018, pp. 200-207, XP085355489, ISSN: 0142-9612, DOI:10.1016/J.BIOMATERIALS.2018.02.017.

Anonymous: "Lumason—Prescribing Information"; Dec. 1, 2016, XP055867615, Retrieved from the Internet: URL: https://www.accessdata.fda.gov/drugsatfda_docs/label/2016/203684s0021b1.pdf.

Anonymous: "DEFNITY—Prescribing Information", Aug. 1, 2011, xp055867617, Retrieved from the Internet: URL: https://www.accessdata.fda.gov/drugsatfda_docs/label/2011/021064s0111b1.pdf.

Applicant: Case Western Reserve University; "Stabilized Nanobubbles and Microbubbles for Diagnostic and Therapeutic Applications"; European Application No. EP19777597; Examiner: Barbara Bliem; Dec. 2, 2021; 12 pgs.

Applicant: Case Western Reserve University; "Stabilized Cross-linked Nanobibbles for Diagnostic and Therapeutic Application" U.S. Appl. No. 16/306,840, filed Dec. 3, 2018; Office Action dated Sep. 30, 2022; 20 pgs.

Perera Reshani et al: "Nanobubble Extravasation in Prostate Tumors Imaged with Ultrasound: Role of Active versus Passive Targeting", 2018 IEEE International Ultrasonics Symposium (IUS), IEEE, Oct. 22, 2018 (Oct. 22, 2018), pp. 1-4.

* cited by examiner

| Reagents (for 5 mL solution) | Pure PG (Control 1) | PG/Gly (Product) | Pure Gly (Control 2) | Pure PBS (Control 3) |
|---|---|---|---|---|
| C22 (DBPC) | 30.5 mg | 30.5 mg | 30.5 mg | 30.5 mg |
| DPPA | 5.0 mg | 5.0 mg | 5.0 mg | 5.0 mg |
| DPPE | 10.0 mg | 10.0 mg | 10.0 mg | 10.0 mg |
| DSPE-mPEG 2000 | 5.0 mg | 5.0 mg | 5.0 mg | 5.0 mg |
| PBS | 4.0 mL | 4.0 mL | 4.0 mL | 5.0 mL |
| **Glycerol** | **0** | **0.5 mL** | **1.0 mL** | **0 mL** |
| **Propylene Glycol** | **1.0 mL** | **0.5 mL** | **0 mL** | **0 mL** |

(a)

(b)

(a)

(b)

(a)

(b)

(C)

C.

d.

STABILIZED NANOBUBBLES AND MICROBUBBLES FOR DIAGNOSTIC AND THERAPEUTIC APPLICATIONS

RELATED APPLICATION

This application claims priority from U.S. Provisional Application No. 62/650,178, filed Mar. 29, 2018, the subject matter of which is incorporated herein by reference in its entirety.

GOVERNMENT FUNDING

This invention was made with government support under W81XWH-16-1-0371 awarded by the Department of Defense. The government has certain rights in the invention.

TECHNICAL FIELD

This application relates to diagnostic and therapeutic compositions, and more particularly to stabilized nanobubbles and microbubbles for diagnostic, therapeutic, and theranostic applications.

BACKGROUND

Ultrasound contrast agents (UCA) are small gas-filled bubbles with a stabilizing shell made from a variety of materials, such as polymer, protein or lipid. Other than the traditional applications of these agents in diagnostic ultrasound imaging, UCA have found relevance in therapeutic applications including targeted gene and drug delivery. These adaptable particles are currently being explored as protective therapeutic carriers and as cavitation nuclei to enhance delivery of their payload by sonoporation. Together these functions improve payload circulation half-life and release profiles as well as tissue selectivity and cell uptake. Regardless of the mode of action, it is advantageous, particularly in cancer therapy, for the bubbles to extravasate from the vasculature and arrive at the cellular target site for the desired effect.

Commercial UCA available today are typically designed to serve only as blood pool agents with diameters of 1-8 μm. Although previous methodologies have been developed to reduce bubble size, most of these strategies involve manipulations of microbubbles post formation, such as gradient separation by gravitational forces or by physical filtration or floatation. While effective for selecting nanosized bubbles, these methods typically reduce bubble yield and stability and introduce potential for sample contamination in addition to being labor intensive. Additionally, the applicability of microbubbles as carriers (e.g., in cancer therapy) and molecular imaging contrast agents (e.g. in identifying biomarkers on cell surface) has been limited by a large size, which typically confines them to the vasculature and does not enable them to come in direct contact with the target cells.

SUMMARY

Embodiments described herein relate to long-circulating, stabilized nanobubbles and microbubbles for diagnostic and therapeutic applications. The stabilized nanobubbles and microbubbles can be used as multifunctional and/or theranostic platforms for routine contrast-enhanced ultrasound imaging, ultrasound molecular imaging, drug therapy, gene therapy, chemotherapy, and anti-microbial applications.

Each stabilized nanobubble and/or microbubble can include a lipid membrane or shell that defines an internal space or volume. The internal space can include at least one gas. The lipid membrane can include a plurality of lipids, at least one edge-activator, which is incorporated between lipids of the membrane and enhances the flexibility of the nanobubble, and a membrane stiffener, which is incorporated on and/or in an outer surface of the membrane and enhances the membrane resistance to tearing.

Advantageously, the stabilized nanobubbles and microbubbles described herein can be formulated as ultrasound contrast agent that are visible with clinically available nonlinear (contrast) ultrasound imaging sequences at frequencies of about 1 MHz to about 50 MHz (e.g., about 3 MHz to about 18 MHz). The stabilized nanobubbles can be on an order of magnitude smaller in diameter (e.g., about 300 nm vs. about 3000 nm for commercial microbubbles), and the nanobubbles and microbubbles can be about 12 to about 20 times more stable (in terms of in vivo circulation time) than commercially available microbubbles. The stabilized nanobubbles can enhance the contrast of ultrasound images of the vascular capillary bed as their smaller size and higher number density enables them to reach smaller blood vessels in sufficient concentration, resulting in superb image quality without significant signal attenuation (which is a problem with larger microbubbles at higher concentrations). Nanobubbles can extravasate beyond hyperpermeable vasculature into the tissue parenchyma in tumors or other pathologies exemplified by inflammation and hallmarked by vascular hyperpermeability (such as type 1 diabetes and kidney fibrosis). The tissue enhancement in nonlinear ultrasound imaging modes using the nanobubbles can result in much improved image contrast intravascularly in addition to extravascularly.

The stabilized nanobubbles and microbubbles can have a lipid concentration that enhances the in vivo circulation stability of the nanobubbles and microbubbles. It was found that a higher lipid concentration correlated with an increase in stability and longer circulation of the nanobubbles and microbubbles upon administration to a subject. In some embodiments, the stabilized nanobubbles and microbubbles can have a lipid concentration of at least about 2 mg/ml, at least about 3 mg/ml, at least about 4 mg/ml, at least about 5 mg/ml, about 6 mg/ml, at least about 7 mg/ml, at least about 8 mg/ml, at least about 9 mg/ml, at least about 10 mg/ml, at least about 11 mg/ml, at least about 12 mg/ml or more. In other embodiments, the lipid concentration of the stabilized nanobubbles and microbubbles can be about 5 mg/ml to about 12 mg/ml, about 6 mg/ml to about 12 mg/ml, about 7 mg/ml to about 12 mg/ml, about 8 mg/ml to about 12 mg/ml, about 9 mg/ml to about 12 mg/ml, about 10 mg/ml to about 12 mg/ml, or at least about 10 mg/ml.

In some embodiments, the plurality of lipids used to form the membrane can include a mixture of phospholipids having varying acyl chain lengths. For example, the lipids can include a mixture of at least two of dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In other embodiments, the mixture of phospholipids having varying acyl chain length can include dibehenoylglycerophosphocoline (DBPC) and one or more additional phospholipids selected from the group consisting of dipalmitoylphosphatidylcholine (DPPC), distearoylphosphatidylcholine (DSPC), diarachidonylphosphatidylcholine (DAPC), dioleoylphosphatidylethanolamine (DOPE), dipalmitoylphosphatidylethanolamine (DPPE), distearoylphosphatidylethanolamine (DSPE), dipalmitoylphosphatidic acid (DPPA), or PEG functionalized phospholipids thereof. The PEG can have a molecular weight of about 1000 to about 5000 Da, for example, about 2000 Da.

In some embodiments, the mixture of phospholipids can include at least about 40%, at least about 50%, at least about 60%, at least about 70%, or at about 80%, by weight of dibehenoylglycerophosphocoline (DBPC); and less than about 60%, less than about 50%, less than about 40%, less than about 30%, or less than about 20%, by weight, of a combination of additional phospholipids selected from the group consisting of dipalmitoylphosphatidylcholine (DPPC), distearoylphosphatidylcholine (DSPC), diarachidonylphosphatidylcholine (DAPC), dioleoylphosphatidylethanolamine (DOPE), dipalmitoylphosphatidylethanolamine (DPPE), distearoylphosphatidylethanolamine (DSPE), dipalmitoylphosphatidic acid (DPPA), or PEG functionalized phospholipids thereof.

In some embodiments, the mixture of phospholipids can include about 40% to about 80%, about 50% to about 70%, or about 55% to about 65% (e.g., about 60%) by weight dibehenoylglycerophosphocoline (DBPC); and about 20% to about 60%, about 30% to about 50%, or about 35% to about 45% (e.g., about 40%) by weight of a combination of additional phospholipids selected from the group consisting of dipalmitoylphosphatidylcholine (DPPC), distearoylphosphatidylcholine (DSPC), diarachidonylphosphatidylcholine (DAPC), dioleoylphosphatidylethanolamine (DOPE), dipalmitoylphosphatidylethanolamine (DPPE), distearoylphosphatidylethanolamine (DSPE), dipalmitoylphosphatidic acid (DPPA), or PEG functionalized phospholipids thereof.

In other embodiments, the one or more additional phospholipids can include, consist essentially of, or consists of a combination of dipalmitoylphosphatidic acid (DPPA), dipalmitoylphosphatidylethanolamine (DPPE), and PEG functionalized distearoylphosphatidylethanolamine (DSPE).

In still other embodiments, the mixture of phospholipids can include dibehenoylglycerophosphocoline (DBPC), dipalmitoylphosphatidic acid (DPPA), dipalmitoylphosphatidylethanolamine (DPPE), and PEG functionalized distearoylphosphatidylethanolamine (DSPE) at a ratio of, for example, about 6:1:1:1.

In some embodiments, the edge-activator, which is incorporated between lipids of the membrane of each nanobubble or microbubble and enhances the flexibility of the nanobubbles can include a co-surfactant, such as propylene glycol, which enhances the effectiveness of phospholipid surfactants. Other edge activators, which can be substituted for propylene glycol or used in combination with propylene glycol, can include cholesterol, sodium cholate, limonene, oleic acid, and/or span 80. The edge activator can be provided in each of the nanobubbles at an amount effective to cause separation of lipid domains of the nanobubble and form defects that absorb excessive pressure, which could have caused lipid "domain" tearing.

In some embodiments, the amount of propylene glycol provided in the nanobubbles and microbubbles can be about 0.05 ml to about 0.5 ml, about 0.06 ml to about 0.4 ml, about 0.07 ml to about 0.3 ml, about 0.08 ml to about 0.2 ml, or about 0.1 ml, per 1 ml of hydrated lipids.

In other embodiments, a membrane stiffener, which is incorporated on an outer surface of the membrane of each nanobubble or microbubble and enhances the membranes resistance to tearing, includes glycerol. Glycerol can be provided on the membrane of each nanobubble or microbubble at an amount effective to stiffen the membrane and improve the membrane's resistance to lipid "domain" tearing. The amount of glycerol provided on the membranes of the nanobubbles and microbubbles can be about 0.05 ml to about 0.5 ml, about 0.06 ml to about 0.4 ml, about 0.07 ml to about 0.3 ml, about 0.08 ml to about 0.2 ml, or about 0.1 ml, per 1 ml of hydrated lipids.

In some embodiments, each of the nanobubbles or microbubbles can include a hydrophilic outer domain at least partially defined by hydrophilic heads of the lipid and a hydrophobic inner domain at least partially defined by hydrophobic tails of the lipid. An edge activator, such as propylene glycol, can at least partially extend between the lipids from the outer domain to the inner domain. The glycerol can be provided on the outer domain of the nanobubbles and extend partially between hydrophilic heads of the lipids. The gas, which is encapsulated by the membrane, can have a low solubility in water (e.g., hydrophobic gas) and include, for example, a perfluorocarbon, such as perfluoropropane or perfluorobutane, sulfur hexafluoride, carbon dioxide, nitrogen ($N_2$), oxygen ($O_2$), and/or air.

In some embodiments, each of the nanobubbles can have a size that facilitates extravasation of the nanobubble in cancer therapy or diagnosis. For example, the nanobubble can have a diameter or size of about 30 nm to about 600 nm (or about 50 nm to about 500 nm or about 100 nm to about 400 nm).

In other embodiments, each of the microbubbles can have a diameter or size of about 1 μm to about 8 μm (or about 1 μm to about 5 μm or about 5 μm to about 8 μm).

In a further aspect, the nanobubbles and microbubbles can include at least one targeting moiety that is linked to the membrane. The targeting moiety can be selected from the group consisting of polypeptides, polynucleotides, small molecules, elemental compounds, antibodies, and antibody fragments.

In a still further aspect, the nanobubble and microbubbles can include cargo, such as at least one therapeutic agent, that is contained within the membrane or conjugated to the membrane of each nanobubble or microbubble. The nanobubble and microbubbles can be used to carry or deliver the cargo (e.g., therapeutic agent) at an increased concentration with extended in vivo circulation time and can be destroyed with ultrasound on demand to increase cargo delivery efficiency. For example, the cargo can be a small molecule drug, antibody, peptide, DNA, RNA, and/or siRNA, such as a chemotherapeutic agent, anti-proliferative agent, biocidal agent, biostatic agent, or anti-microbial agent.

Other embodiments described herein relate to a method for forming a composition comprising at least one stabilized nanobubble and/or microbubble. The method can include the steps of: (a) dissolving the mixture of lipids in propylene glycol; (b) adding a mixture of glycerol and phosphate buffered solution (PBS) to the lipid propylene glycol mixture; optionally (d) removing air and injecting gas, such as perfluoropropane, perfluorobutane, sulfur hexafluoride, carbon dioxide, nitrogen ($N_2$), and oxygen ($O_2$), to replace the air in a vial containing the mixture lipids/propylene glycol/glycerol/PBS, and (e) shaking the mixture of the lipids/propylene glycol/glycerol/PBS to form at least one nanobubble and/or microbubble.

A further embodiment described herein relates to a method for imaging a region of interest (ROI) in a subject.

The method can include administering to the subject a composition comprising a plurality of stabilized nanobubbles and/or microbubbles. Each of the nanobubbles or microbubbles can have a lipid membrane that defines an internal space that encapsulates or contains at least one gas. The lipid membrane can include a plurality of lipids, at one activator edge-activator, which is incorporated between lipids of the membrane and enhances the flexibility of the nanobubbles, and a membrane stiffener, which is incorporated on an outer surface of the membrane and enhances the membranes resistance to tearing. After administering the composition to the subject, at least one image of the ROI can be generated.

A further aspect of the application relates to a method for treating a neoplastic disorder in a subject. The method can include administering to neoplastic cells of the subject a composition comprising a plurality of stabilized nanobubbles and/or microbubbles. Each of the nanobubbles or microbubbles can have a lipid membrane that defines an internal space that encapsulates or contains at least one gas. The lipid membrane can include a plurality of lipids, at least one edge-activator, which is incorporated between lipids of the membrane and enhances the flexibility of the nanobubbles, and a membrane stiffener, which is incorporated on an outer surface of the membrane and enhances the membranes resistance to tearing. A chemotherapeutic agent can be provided on or in the nanobubble.

Ultrasound can then be applied to a region of interest of the subject that includes the neoplastic cells and nanobubbles and/or microbubbles to cause release of the chemotherapeutic agent from the nanobubbles and/or microbubbles in the region of interest to the neoplastic cells.

Still other embodiments described herein relate to a method of assessing vascular permeability of vasculature of a subject in need thereof. The method can include administering to the subject a composition comprising a plurality of stabilized nanobubbles. Each of the nanobubbles can have a lipid membrane that defines an internal space that encapsulates or contains at least one gas. The lipid membrane can include a plurality of lipids, at one activator edge-activator, which is incorporated between lipids of the membrane and enhances the flexibility of the nanobubbles, and a membrane stiffener, which is incorporated on an outer surface of the membrane and enhances the membranes resistance to tearing. After administering the composition to the subject, at least one intravascular and/or extravascular ultrasound image can be generated to determine extravasation of the nanobubbles and permeability of the vasculature.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
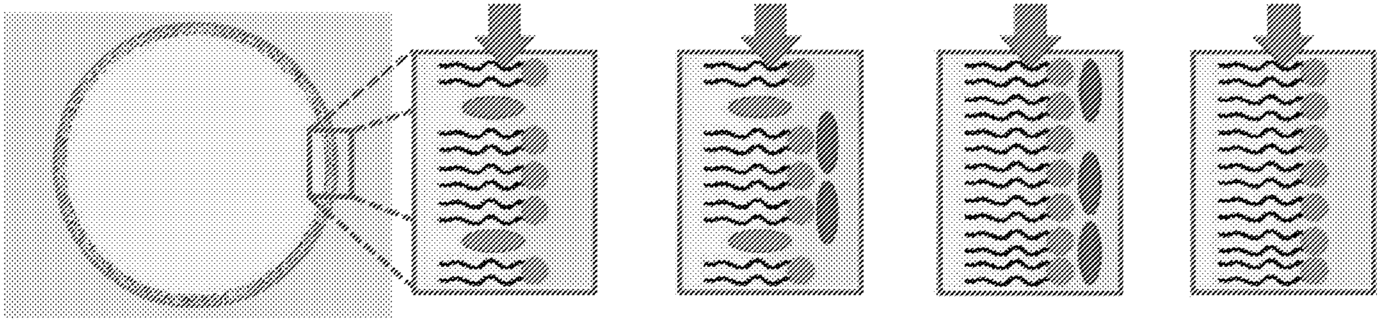
FIG. 1 illustrates a table and schematic showing nanobubble formulations and lipid membrane configurations.

All scientific and technical terms used in this application have meanings commonly used in the art unless otherwise specified. The definitions provided herein are to facilitate understanding of certain terms used frequently herein and are not meant to limit the scope of the application.

The term "neoplastic disorder" can refer to a disease state in a subject in which there are cells and/or tissues which proliferate abnormally. Neoplastic disorders can include, but are not limited to, cancers, sarcomas, tumors, leukemias, lymphomas, and the like.

The term "neoplastic cell" can refer to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

The term "tumor" can refer to an abnormal mass or population of cells that result from excessive cell division, whether malignant or benign, and all pre-cancerous and cancerous cells and tissues.

The terms "treating" or "treatment" of a disease (e.g., a neoplastic disorder) can refer to executing a treatment protocol to eradicate at least one neoplastic cell. Thus, "treating" or "treatment" does not require complete eradication of neoplastic cells.

The term "polymer" can refer to a molecule formed by the chemical union of two or more chemical units. The chemical units may be linked together by covalent linkages. The two or more combining units in a polymer can be all the same, in which case the polymer may be referred to as a homopolymer. The chemical units can also be different and, thus, a polymer may be a combination of the different units. Such polymers may be referred to as copolymers.

The term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment.

Embodiments described herein relate to stabilized nanobubbles and microbubbles for diagnostic and therapeutic applications. The stabilized nanobubbles and microbubbles can be used as multifunctional and/or theranostic platforms for molecular imaging, drug therapy, gene therapy, chemotherapy, and anti-microbial applications. Each stabilized nanobubble or microbubble can include a modified lipid and edge-activator enriched shell or membrane encapsulating a gas. The stabilized nanobubbles and microubbbles are resilient to destruction and collapse at higher applied acoustic pressures and can circulate for over 12 times longer compared to clinical microbubbles (Lumason) in vivo without decay.

The membranes of the stabilized nanobubbles and microbubbles described herein are tightly packed permitting a smaller size than traditionally formed microbubbles. The stabilized nanobubbles and microbubbles described herein are much more flexible than traditionally formed microbubbles as result of the edge-activator, which acts as a linker packed between lipids.

Advantageously, the stabilized nanobubbles and microbubbles described herein can be formulated as ultrasound contrast agent that are visible with clinically available nonlinear (contrast) ultrasound imaging sequences at frequencies of about 1 MHz to about 50 MHz (e.g., about 3 MHz to about 18 MHz). The stabilized nanobubbles can be on an order of magnitude smaller in diameter (e.g., about 300 nm vs. about 3000 nm for commercial microbubbles), and the nanobubbles and microbubbles can be about 12 to about 20 times more stable (in terms of in vivo circulation time) than commercially available microbubbles. The stabilized nanobubbles can enhance the contrast of ultrasound images of the vascular capillary bed as their smaller size and higher number density enables them to reach smaller blood vessels in sufficient concentration, resulting in superb image quality without significant signal attenuation (which is a problem with larger microbubbles at higher concentrations). Nanobubbles can extravasate beyond hyperpermeable vasculature into the tissue parenchyma in tumors or other pathologies exemplified by inflammation and hallmarked by vascular hyperpermeability (such as type 1 diabetes and kidney fibrosis). The tissue enhancement in nonlinear ultrasound imaging modes using the nanobubbles can result in much improved image contrast intravascularly in addition to extravascularly.

Additionally, the lipid shell of the nanobubbles and microbubbles also allow therapeutic agents and targeting moieties to be linked to, conjugated to, or encapsulated by the nanobubbles and microbubbles. This permits the nanobubbles and microbubbles to be used as delivery vehicles in therapeutic applications as well as provides active targeting of the nanobubbles and microbubbles to the tissue or cells being treated.

Each of the stabilized nanobubble or microbubbles can include a lipid membrane or shell that defines an internal space. The internal space can include at least one gas. The lipid membrane can include a plurality of lipids, an edge-activator, which is incorporated between lipids of the membrane and enhances the flexibility of the nanobubbles and microbubbles, and a membrane stiffener, which is incorporated on an outer surface of the membrane and enhances the membranes resistance to tearing.

In some embodiments, each of the nanobubbles or microbubbles can include a hydrophilic outer domain at least partially defined by hydrophilic heads of the lipid and a hydrophobic inner domain at least partially defined by hydrophobic tails of the lipid. An edge activator, such as propylene glycol, can at least partially extend between the lipids from the outer domain to the inner domain. The glycerol can be provided on the outer domain of the nanobubbles and extend partially between hydrophilic heads of the lipids. The gas, which is encapsulated by the membrane, can have a low solubility in water (e.g., hydrophobic gas) and include, for example, a perfluorocarbon, such as perfluoropropane or perfluorobutane, sulfur hexafluoride, carbon dioxide, nitrogen ($N_2$), oxygen ($O_2$), and air The nanobubbles and microbubbles described herein can have enhanced nanobubble or microbubble stability compared to prior art microbubbles. "Nanobubble stability" or "microbubble stability" can generally refer to the amount of a signal can be obtained when the nanobubble or microbubble is continuously insonated (in vitro) or continuously imaged (in vivo).

In some embodiments, each of the nanobubbles can have a size that facilitates extravasation of the nanobubble in cancer therapy or diagnosis. For example, each of the nanobubbles can have a size (diameter) of about 30 nm to about 600 nm or about 100 nm to about 500 nm (e.g., about 300 nm), depending upon the particular lipids, edge activator, and membrane stiffener as well as the method used to form the nanobubble (described in greater detail below).

In other embodiments, each of the microbubbles can have a diameter or size of about 1 μm to about 8 μm (or about 1 μm to about 5 μm or about 5 μm to about 8 μm).

The stabilized nanobubbles and microbubbles can have a lipid concentration that enhances the in vivo circulation stability of the nanobubbles and microbubbles. It was found that a higher lipid concentration correlated with an increase in stability and longer circulation of the nanobubbles and microbubbles upon administration to a subject. In some embodiments, the stabilized nanobubbles and microbubbles can have a lipid concentration of at least about 2 mg/ml, at least about 3 mg/ml, at least about 4 mg/ml, at least about 5 mg/ml, about 6 mg/ml, at least about 7 mg/ml, at least about 8 mg/ml, at least about 9 mg/ml, at least about 10 mg/ml, at least about 11 mg/ml, at least about 12 mg/ml or more. In other embodiments, the lipid concentration of the stabilized nanobubbles and microbubbles can be about 5 mg/ml to about 12 mg/ml, about 6 mg/ml to about 12 mg/ml, about 7 mg/ml to about 12 mg/ml, about 8 mg/ml to about 12 mg/ml, about 9 mg/ml to about 12 mg/ml, about 10 mg/ml to about 12 mg/ml, or at least about 10 mg/ml.

The plurality of lipids comprising the membrane or shell can include any naturally-occurring, synthetic or semi-synthetic (i.e., modified natural) moiety that is generally amphipathic or amphiphilic (i.e., including a hydrophilic component and a hydrophobic component). Examples of lipids, any one or combination of which may be used to form the membrane, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), dibehenoylglycerophosphocoline (DBPC), distearoylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; phospholipids with medium chain fatty acids of about 10 to about 16 carbons in length; phospholipids with long chain fatty acids of about 18 to about 24 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, DE), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl) carbonyl)methylamino)octadecanoic acid; N-[12-(((7'-diethylaminocoumarin-3-yl)carbonyl)methylamino) octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof.

In some embodiments, the plurality of lipids used to form the membrane can include a mixture of phospholipids having varying acyl chain lengths. For example, the lipids can include a mixture of at least two of dipalmitoylphosphatidylcholine (DPPC), dibehenoylglycerophosphocoline (DBPC), distearoylphosphatidylcholine (DSPC), diarachidonylphosphatidylcholine (DAPC), dioleoylphosphatidylethanolamine (DOPE), dipalmitoylphosphatidylethanolamine (DPPE), and distearoylphosphatidylethanolamine (DSPE); dipalmitoylphosphatidic acid (DPPA), or PEG functionalized lipids thereof.

In other embodiments, the mixture of phospholipids having varying acyl chain length can include dibehenoylglycerophosphocoline (DBPC) and one or more additional phospholipids selected from the group consisting of dipalmitoylphosphatidylcholine (DPPC), distearoylphosphatidylcholine (DSPC), diarachidonylphosphatidylcholine (DAPC), dioleoylphosphatidylethanolamine (DOPE), dipalmitoylphosphatidylethanolamine (DPPE), distearoylphosphatidylethanolamine (DSPE), dipalmitoylphosphatidic acid (DPPA), or PEG functionalized phospholipids thereof.

In some embodiments, the mixture of phospholipids can include at least about 40%, at least about 50%, at least about 60%, at least about 70%, or at about 80%, by weight of dibehenoylglycerophosphocoline (DBPC); and less than about 60%, less than about 50%, less than about 40%, less than about 30%, or less than about 20%, by weight, of a combination of additional phospholipids selected from the group consisting of dipalmitoylphosphatidylcholine (DPPC), distearoylphosphatidylcholine (DSPC), diarachidonylphosphatidylcholine (DAPC), dioleoylphosphatidylethanolamine (DOPE), dipalmitoylphosphatidylethanolamine (DPPE), distearoylphosphatidylethanolamine (DSPE), dipalmitoylphosphatidic acid (DPPA), or PEG functionalized phospholipids thereof. The PEG can have a molecular weight of about 1000 to about 5000 Da, for example, about 2000 Da.

In some embodiments, the mixture of phospholipids can include about 40% to about 80%, about 50% to about 70%, or about 55% to about 65% (e.g., about 60%) by weight dibehenoylglycerophosphocoline (DBPC); and about 20% to about 60%, about 30% to about 50%, or about 35% to about 45% (e.g., about 40%) by weight of a combination of additional phospholipids selected from the group consisting of dipalmitoylphosphatidylcholine (DPPC), distearoylphosphatidylcholine (DSPC), diarachidonylphosphatidylcholine (DAPC), dioleoylphosphatidylethanolamine (DOPE), dipalmitoylphosphatidylethanolamine (DPPE), distearoylphosphatidylethanolamine (DSPE), dipalmitoylphosphatidic acid (DPPA), or PEG functionalized phospholipids thereof.

In other embodiments, the one or more additional phospholipids can include, consist essentially of, or consists of a combination of dipalmitoylphosphatidic acid (DPPA), dipalmitoylphosphatidylethanolamine (DPPE), and PEG functionalized distearoylphosphatidylethanolamine (DSPE).

In still other embodiments, the mixture of phospholipids can include dibehenoylglycerophosphocoline (DBPC), dipalmitoylphosphatidic acid (DPPA), dipalmitoylphosphatidylethanolamine (DPPE), and PEG functionalized distearoylphosphatidylethanolamine (DSPE) at a ratio of, for example, about 6:1:1:1 by weight.

In some embodiments, the edge-activator, which is incorporated between lipids of the membrane of each nanobubble or microbubble and enhances the flexibility of the nanobubbles can include a co-surfactant, such as propylene glycol, which enhances the effectiveness of phospholipid surfactants. The edge activator can be provided in each of the nanobubbles at an amount effective to cause separation of lipid domains of the nanobubble and form defects that absorb excessive pressure, which could have caused lipid "domain" tearing. Other edge activators, which can be substituted for propylene glycol or used in combination with propylene glycol, can include cholesterol, sodium cholate, limonene, oleic acid, and/or span 80.

In some embodiments, the amount of propylene glycol provided in the nanobubbles can be about 0.05 ml to about 0.5 ml, about 0.06 ml to about 0.4 ml, about 0.07 ml to about 0.3 ml, about 0.08 ml to about 0.2 ml, or about 0.1 ml, per 1 ml of hydrated lipids.

In other embodiments, a membrane stiffener, which is incorporated on the outer surface of the membrane of each nanobubble or microbubble and enhances the membranes resistance to tearing, includes glycerol. Glycerol can be provided on the membrane of each of the nanobubbles or microbubble at an amount effective to stiffen the membrane and improve the membrane's resistance to lipid "domain" tearing. The amount of glycerol provided on the membranes of the nanobubbles and microbubbles can be about 0.05 ml to about 0.5 ml, about 0.06 ml to about 0.4 ml, about 0.07 ml to about 0.3 ml, about 0.08 ml to about 0.2 ml, or about 0.1 ml, per 1 ml of hydrated lipids.

The membranes defining the nanobubbles and microbubbles can be concentric or otherwise and have a unilamellar configuration (i.e., comprised of one monolayer or bilayer), an oligolamellar configuration (i.e., comprised of about two or about three monolayers or bilayers), or a multilamellar configuration (i.e., comprised of more than about three monolayers or bilayers). The membrane can be substantially solid (uniform), porous, or semi-porous.

The internal void space by the membrane can include at least one gas. The gas can have a low solubility in water and be, for example, a perfluorocarbon, such as perfluoropropane (e.g., octafluoropropane or perfluorobutane). The internal void can also include other gases, such as carbon dioxide, sulfur hexafluoride, air, nitrogen ($N_2$), oxygen ($O_2$), and helium.

In some embodiments, the nanobubbles and microbubbles can include a linker to link a targeting moiety and/or bioactive agent to the membrane of each nanobubble. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

The stabilized nanobubbles and microbubbles can also include other materials, such as liquids, oils, bioactive agents, diagnostic agents, therapeutic agents, photoacoustic agents (e.g., sudan black), and/or nanoparticles (e.g., iron oxide). The materials can be encapsulated by the membrane and/or linked or conjugated to the membrane.

Bioactive agents encapsulated by and/or linked to the membrane can include any substance capable of exerting a biological effect in vitro and/or in vivo. Examples of bioactive agents can include, but are not limited to, chemotherapeutic agents, biologically active ligands, small molecules, DNA fragments, DNA plasmids, interfering RNA molecules, such as siRNAs, oligonucleotides, and DNA encoding for shRNA. Diagnostic agents can include any substance that may be used for imaging a region of interest (ROI) in a subject and/or diagnosing the presence or absence of a disease or diseased tissue in a subject. Therapeutic agents can refer to any therapeutic or prophylactic agent used in the treatment (including the prevention, diagnosis, alleviation, or cure) of a malady, affliction, condition, disease or injury in a subject. It will be appreciated that the membrane can additionally or optionally include proteins, carbohydrates, polymers, surfactants, and/or other membrane stabilizing materials, any one or combination of which may be natural, synthetic, or semi-synthetic.

In some embodiments, the bioactive agent can include a therapeutic agent, such as a chemotherapeutic agent, an anti-proliferative agent, an anti-microbial agent, a biocidal agent, and/or a biostatic agent. The therapeutic agent can be encapsulated by and/or linked to the membrane of the nanobubble or microbubble.

In some embodiments, the membrane can additionally or optionally include at least one targeting moiety that is capable of targeting and/or adhering the nanobubble or microbubble to a cell or tissue of interest. In some embodiments, the targeting moiety can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting moiety can interact with include molecules associated with a particular disease. For example, the biomarkers can include cell surface receptors implicated in cancer development, such as CA-125 receptor, epidermal growth factor receptor, and transferrin receptor. The targeting moiety can interact with the biomarkers through non-covalent binding, covalent binding, hydrogen binding, van der Waals forces, ionic bonds, hydrophobic interactions, electrostatic interaction, and/or combinations thereof.

The targeting moiety can include, but is not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can comprise an antibody, such as a monoclonal antibody, a polyclonal antibody, or a humanized antibody, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ($(scFv)_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating antibodies. These methods typically include the step of immunization of animals, typically mice, with a desired immunogen (e.g., a desired target molecule or fragment thereof). Once the mice have been immunized, and boosted one or more times with the desired immunogen(s), antibody-producing hybridomas may be prepared and screened according to well-known methods. See, for example, Kuby, Janis, Immunology, Third Edition, pp. 131-139, W.H. Freeman & Co. (1997), for a general overview of monoclonal antibody production, that portion of which is incorporated herein by reference.

The targeting moiety need not originate from a biological source. The targeting moiety may, for example, be screened from a combinatorial library of synthetic peptides. One such method is described in U.S. Pat. No. 5,948,635, incorporated herein by reference, which describes the production of phagemid libraries having random amino acid insertions in the pIII gene of M13. This phage may be clonally amplified by affinity selection.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting moiety may be modified to make them more resistant to cleavage by proteases. For example, the stability of targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

In certain embodiments, the antibodies or variants thereof may be modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), Nature, 321, 522-525 or Tempest et al. (1991), Biotechnology, 9, 266-273. Also, transgenic mice, or other mammals, may be used to express humanized antibodies. Such humanization may be partial or complete.

In certain embodiments, a targeting moiety as described herein may comprise a homing peptide, which selectively directs the nanobubble to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting moiety may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In other embodiments, the targeting moiety may comprise a ligand molecule, including, for example, ligands which naturally recognize a specific desired receptor of a target cell. Such ligand molecules include ligands that have been modified to increase their specificity of interaction with a target receptor, ligands that have been modified to interact with a desired receptor not naturally recognized by the ligand, and fragments of such ligands.

In still other embodiments, the targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting moiety may be a peptidomimetic. By employing, for example, scanning mutagenesis to map the amino acid residues of a protein, which is involved in binding other proteins, peptidomimetic compounds can be generated that mimic those residues, which facilitate the interaction. Such mimetics may then be used as a targeting moiety to deliver the nanobubble to a target cell. For instance, non-hydrolyzable peptide analogs of such resides can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

By way of example, where the cell targeted comprises an ovarian cancer cell, the targeting moiety can comprise an antibody or peptide to human CA-125R. Over expression of CA-125 has implication in ovarian cancer cells. Alternatively, where the cell targeted comprises a malignant cancer, such as glioblastoma, the targeting moiety can comprise an antibody or peptide to extracellular growth factor receptor (EGFR) and/or human transferrin receptor (TfR). Overexpression of EGFR and TfR has been implicated in the malignant phenotype of tumor cells. The overexpression of these receptors also leads to activation of other genes that promote cancer growth through such means as invasion and metastasis, as well as resistance to chemotherapy and radiotherapy. The imaging of cancer cells expressing EGFR and TfR can provide a molecular signature of the malignancy or progression of such cells.

The membrane also includes at least one PSMA targeting moiety or PSMA ligand that can selectively recognize PSMA-expressing tumors, cancer cells, and/or cancer neovasculature in vivo. PSMA is a transmembrane protein that is highly overexpressed (100-1000 fold) on almost all prostate cancer (PC) tumors. Only 5-10% of primary PC lesions have been shown to be PSMA-negative. PSMA expression levels increase with higher tumor stage and grade.

Small molecule PSMA ligands bind to the active site in the extracellular domain of PSMA and are internalized and endosomally recycled, leading to enhanced tumor uptake and retention and high image quality. Examples of PSMA ligands are described in Afshar-Oromieh A, Malcher A, Eder M, et al. PET imaging with a [68Ga]gallium-labelled PSMA ligand for the diagnosis of prostate cancer: biodistribution in humans and first evaluation of tumour; Weineisen M, Schottelius M, Simecek J, et al. 68Ga- and 177Lu-Labeled PSMA I&T: Optimization of a PSMA-Targeted Theranostic Concept and First Proof-of-Concept Human Studies. *J Nucl Med.* 2015; 56:1169-1176. lesions. *Eur J Nucl Med Mol Imaging.* 2013; 40:486-495; Cho S Y, Gage K L, Mease R C, et al. Biodistribution, tumor detection, and radiation dosimetry of 18F-DCFBC, a low-molecular-weight inhibitor of prostate-specific membrane antigen, in patients with metastatic prostate cancer. *J Nucl Med.* 2012; 53:1883-1891; and Rowe S P, Gage K L, Faraj S F, et al. (1)(8)F-DCFBC PET/CT for PSMA-Based Detection and Characterization of Primary Prostate Cancer. *J Nucl Med.* 2015; 56:1003-1010.

Other examples of PSMA ligands are described in U.S. Pat. Nos. 6,875,886, 6,933,114, and 8,609,142, which are incorporated herein by reference in their entirety. Still other examples PSMA ligands are disclosed in U.S. Patent Application Publication No. 2015/0366968, U.S. Patent Application Publication No. 2015/0366968, 2018/0064831, 2018/0369385, and U.S. Pat. No. 9,889,199 all of which are incorporated by reference in their entirety.

In some embodiments, the PSMA ligand can have the general formula (I):

(I)

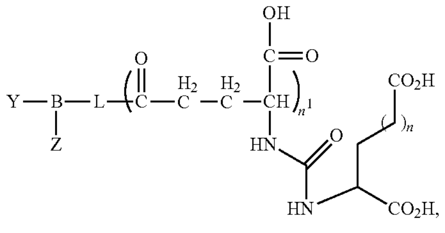

wherein:

n and $n^1$ are each independently 1, 2, 3, or 4;

L is an optionally substituted aliphatic or heteroaliphatic linking group;

B is linker, such as a peptide linker, that includes at least one negatively charged amino acid; and Y is a lipid of the nanobubble or microbubble membrane, which is directly or indirectly linked or coupled to B, and Z is hydrogen or at least one of a detectable moiety or label or a therapeutic agent, which is directly or indirectly linked or coupled to B. In other embodiments, Z can be selected from the group consisting of an imaging agent, an anticancer agent, or a combination thereof. In still other embodiments, Z is a fluorescent label, such as Rhodamine, IRDye700, IRDye800, Cy3, Cy5, and/or Cy5.5.

A composition comprising the at least one stabilized nanobubble and/or microbubble described herein can be readily formulated in two hours without the use of toxic or hazardous solvents, such as chloroform. The stabilized nanobubbles and microbubbles produced by the methodology described are also substantially monodisperse.

In the first step of the method, at least one lipid can be dissolved in propylene glycol to produce a lipid-propylene glycol solution. The lipid(s) dissolved in propylene glycol can include any one or combination of those described above. It will be appreciated that other materials can be dissolved in the propylene glycol, such as proteins, carbohydrates, polymers, surfactants, and/or other membrane stabilizing materials. In one example, the lipids DBPC (1,2-Dibehenoyl-sn-Glycero-3-Phosphocholine), DPPA (1,2 Dipalmitoyl-sn-Glycero-3-Phosphate), DPPE (1,2-dipalmitoyl-sn-glycero-3-phosphoethanolamine) (Avanti Polar Lipids, Pelham, AL), and mPEG-DSPE (1,2-Distearoyl-phosphatidylethanol amine-methyl-poly ethylene glycol conjugate-2000) (Laysan Lipids, Arab, AL) can be dissolved in propylene glycol.

After producing the lipid-propylene glycol solution, a glycerol and phosphate buffered solution (PBS) solution can be added to lipid-propylene glycol solution and the resulting solution can be mixed by, for example, sonication. The mixed solution can be transferred to a vial. The air can removed from the sealed vial containing the hydrated lipid solution and replaced with a gas, such as octafluoropropane, until the vial pressure equalized. The resultant solution can then be shaken or stirred for a time (e.g., about 45 seconds) sufficient to form the nanobubbles. In one example, a lipid-propylene glycol solution comprising DBPC/DPPA/DPPE/mPEG-DSPE dissolved in propylene glycol can be contacted with a hydration PBS/glycerol solution, placed in a vial, and then placed in an incubator-shaker at about 37° C. and at about 120 rpm for about 60 minutes. In some embodiments, the resultant solution containing the nanobubbles can be freeze dried and reconstituted for storage and shipping or frozen and thawed before use.

The stabilized nanobubble and/or microbubble composition so formed can be administered to a subject for diagnostic, therapeutic, and/or theranostic applications. In some embodiments, the nanobubbles and microbubbles can be administered to a subject for imaging at least one region of interest (ROI) of the subject. The ROI can include a particular area or portion of the subject and, in some instances, two or more areas or portions throughout the entire subject. The ROI can include, for example, pulmonary regions, gastrointestinal regions, cardiovascular regions (including myocardial tissue), renal regions, as well as other bodily regions, tissues, lymphocytes, receptors, organs and the like, including the vasculature and circulatory system, and as well as diseased tissue, including neoplastic or cancerous tissue. The ROI can include regions to be imaged for both diagnostic and therapeutic purposes. The ROI is typically internal; however, it will be appreciated that the ROI may additionally or alternatively be external.

In some embodiments, the nanobubbles and microbubbles used to image the ROI can be formulated such that the internal space of at least one of the nanobubbles and/or microbubbles includes at least one contrast agent. For example, a contrast agent (in either liquid or gaseous form) can be contacted with the hydrated lipid/propylene glycol/glycerol solution under conditions effective to entrap the contrast agent in the internal void of the nanobubble. For instance, sealed vials containing a lipid (DBPC/DPPA/DPPE/mPEG-DSPE)/propylene glycol/glycerol solution can have the air withdrawn by a syringe and then octafluoropropane added until the pressure in the vial is equalized. Other examples of contrast agents (besides octafluoropropane) that may be incorporated into the nanobubbles and microbubbles are known in the art and can include stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules.

Since nanobubble and microbubble size may influence biodistribution, the size of the nanobubbles and mcirobubbles can be selected depending upon the region of interest (ROI) of the subject. For a ROI comprising an organ (e.g., a liver or kidney) the size of the nanobubbles and mcirobubbles may be larger than for a ROI comprising tumor tissue. Where the ROI comprises, for example, tumor tissue and differentiation between the tumor tissue and normal or healthy tissue is sought, smaller nanobubbles may be needed to penetrate the smaller venuoles and capillaries comprising the tumor tissue. It should be appreciated that the nanobubbles and microbubbles can comprise additional constituents, such as targeting ligands to facilitate homing of the nanobubbles and microbubbles to the ROI.

The nanobubble and/or microbubble composition can be administered to the subject via any known route, such as via an intravenous injection. By way of example, a composition comprising a plurality of octafluoropropane-containing nanobubbles can be intravenously administered to a subject that is known to or suspected of having a tumor.

At least one image of the ROI can be generated using an imaging modality. The imaging modality can include one or combination of known imaging techniques capable of visualizing the nanobubbles. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET). The imaging modality can then be operated to generate a visible image of the ROI. In a subject known to or suspected of having a tumor, for example, an ultrasonic transducer can be applied to at least a portion of the ROI to image the target tissue. A visible image of the tumor can then be obtained, such that the presence, absence, and/or extent of a particular neoplastic disorder can be ascertained. It will be appreciated that the imaging modality may be used to generate a baseline image prior to administration of the composition. In this case, the baseline and post-administration images can be compared to ascertain the presence, absence, and/or extent of a particular disease or condition.

Still other embodiments described herein relate a method of assessing vascular permeability of vasculature of a subject in need thereof. The method can include administering to the subject a composition comprising a plurality of stabilized nanobubbles. Each of the nanobubbles can have a lipid membrane that defines an internal space that encapsulates or contains at least one gas. The lipid membrane can include a plurality of lipids, at one activator edge-activator, which is incorporated between lipids of the membrane and enhances the flexibility of the nanobubbles, and a membrane stiffener, which is incorporated on an outer surface of the membrane and enhances the membranes resistance to tearing. After administering the composition to the subject, at least one intravascular and/or extravascular ultrasound image can be generated to determine extravasation of the nanobubbles and permeability of the vasculature.

In other embodiments, the nanobubbles and microbubbles can be administered to a subject to treat and/or image a neoplastic disease in subject. Neoplastic diseases treatable by the nanobubbles and microbubbles described herein can include disease states in which there are cells and/or tissues which proliferate abnormally. One example of a neoplastic disease is a tumor. The tumor can include a solid tumor, such as a solid carcinoma, sarcoma or lymphoma, and/or an aggregate of neoplastic cells. The tumor may be malignant or benign, and can include both cancerous and pre-cancerous cells.

A composition comprising the stabilized nanobubbles and/or microbubbles can be formulated for administration (e.g., injection) to a subject diagnosed with at least one neoplastic disorder. The nanobubbles and/or microbubbles can be formulated according to method as described above and include, for example, at least one therapeutic agent or bioactive agent as well as targeting moiety to target the neoplastic cells.

By way of example, the stabilized nanobubbles and/or microbubbles can be targeted to prostate cancer cells by conjugating a PSMA ligand that this is specific for the PSMA antigen that is over expressed on prostate cancer cells. The targeted stabilized nanobubbles and/or microbubbles can be formulated with at least one lipid that is conjugated to PEG. The nanobubbles can then be combined with the PSMA ligand, which will then become conjugated to PEG of the lipid.

The location(s) where the nanobubble and/or microbubble composition is administered to the subject may be determined based on the subject's individual need, such as the location of the neoplastic cells (e.g., the position of a tumor, the size of a tumor, and the location of a tumor on or near a particular organ). For example, the composition may be injected intravenously into the subject. It will be appreciated that other routes of injection may be used including, for example, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal routes.

Since nanobubble and microbubble size may influence biodistribution, the size of the nanobubbles can be selected depending on the neoplastic disorder being imaged and/or treated. Where the neoplastic disorder comprises tumor tissue, smaller nanobubbles may be needed to penetrate the smaller venuoles and capillaries comprising the tumor tissue.

In some embodiments, a drug, bioactive agent and/or therapeutic agent, such as a chemotherapeutic (e.g., doxorubicin) can be loaded into the nanobubble and/or microbubble during nanobubble and/or microbubble formation to provide a stabilized drug loaded nanobubble and/or microbubble. The stabilized drug loaded nanobubble and/or microbubble can be responsive to energy, from a remote source that is effective to release the therapeutic agent from the nanobubble and/or microbubble after administering the nanobubble and/or microbubble to a subject. The remote source can be external or remote from a subject, which allows non-invasive remote release of the therapeutic agent to the subject. Advantageously, nanobubbles and microbubbles that allow remote release of the therapeutic agent, such as a chemotherapeutic agent (e.g., doxorubicin) can target or be targeted to specific cells or tissue of subject, such as tumors, cancers, and metastases, by systemic administration (e.g., intravenous, intravascular, or intraarterial infusion) to the subject and once targeted to the cells or tissue remotely released to specifically treat the targeted cells or tissue of subject (e.g., tumors, cancers, and metastasis). Targeting and selective release of the chemotherapeutic agents to malignant cancer metastases allows treatment of such metastases using chemotherapeutics, which would provide an otherwise negligible effect if not targeted and remotely released using the nanobubbles described herein.

In some embodiments, ultrasound can be used as a remote source to provide locoregional destruction or fragmentation of the nanobubbles and microbubbles to release the therapeutic agent (e.g., chemotherapeutic agent) provided in the nanobubbles and microbubbles to the tissue or region of interest (e.g., cancer or tumor). Advantageously, ultrasound can release the chemotherapeutic agent from the nanobubbles and/or microbubbles and enhance the anti-tumor efficacy chemotherapeutic agent by ultrasonic cavitation effects, sound effect and other effects. The radiation ultrasound also improves the cell membrane permeability of the chemotherapeutic resulting in much more chemotherapeutic agent in the tumor cells.

It will be appreciated that other remote sources can be used to provide locoregional destruction or fragmentation of the nanobubbles and/or microbubbles to release the therapeutic agent. These other remote sources can include, for example, high intensity focused ultrasound (HIFU) and radiofrequency ablation.

The stabilized nanobubbles and/or microbubbles described herein can allow the combination of any of the above noted therapeutic agents and therapies to be administered at a low dose, that is, at a dose lower than has been conventionally used in clinical situations.

A benefit of lowering the dose of the combination therapeutic agents and therapies administered to a subject includes a decrease in the incidence of adverse effects associated with higher dosages. For example, by the lowering the dosage of a chemotherapeutic agent, such as doxorubicin, a reduction in the frequency and the severity of nausea and vomiting will result when compared to that observed at higher dosages. Similar benefits are contemplated for the compounds, compositions, agents and therapies in combination with the nanobubbles and/or microbubbles.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

It will be appreciated that the stabilized nanobubbles and/or microbubbles can be used in other applications besides diagnostic, therapeutic, and theranostic applications described above. Nanobubble ultrasound contrast agents have shown great potential in areas of health including cardiovascular and eye diseases, as well as neuromuscular disorders such as Deschene Muscular dystrophy. Inflammation has been associated with hypoxia. Nanobubbles can deliver oxygen to hypoxic cell and tissues and can be a potential treatment option. In addition, the early stage of atherosclerosis has been manifested with over-expressed intercellular adhesion molecule-1 (ICAM-1), an inflammatory marker. By including ICAM-1 recognizing monoclonal antibodies in the nanobubble membrane or shell, nanobubbles can recognize and adhere to intercellular adhesion molecule-1 (ICAM-1). These types of nanobubble formulations can be used to detect early stages of atherosclerosis, and can be effective in detecting acute cardiac transplant rejection.

Moreover, stabilized nanobubbles and/or microbubbles described herein can also be used for the treatment of Parkinson's disease. In this regard, the nanobubbles can be used to deliver apomorphine, a particularly beneficial but unstable drug for treating Parkinson's disease, through the blood brain barrier.

Although the use of nanobubbles in medicine is in an early development stage, it is possible that in the future, the applications of nanobubbles in medicine will be as far reaching if not more than that of microbubbles whose applications span across the areas of malignant, infectious, cardiovascular and autoimmune diseases.

The following example is for the purpose of illustration only and is not intended to limit the scope of the claims, which are appended hereto.

EXAMPLE

In this Example, we show the development of an ultra-stable shell stabilized nanobubble formulation that has high lipid concentration, contains high molecular weight of polyethylene glycol (PEG), contains high fraction of PEG-functionalized lipid, uses dibehenoylglycerophosphocoline (1,2-dibehenoyl-sn-glycero-3-phosphocholine or DBPC) as the base lipid, and introduces defects in the membrane via inclusion of propylene glycol and glycerol as described below.

To introduce defects in the membrane, we utilized the idea of edge-activators for liposomes. Edge-activators, such as propylene glycol (PG), are co-surfactants that modify the property of the membrane e.g. flexibility. Propylene glycol, in particular, has been shown to make liposome "ultraflexible" enabling it to deform as it passes through a narrow channel (e.g., skin pore) and reform without disruption of its vesicular structure. Glycerol (Gly), on the other hand, has been shown to stiffen the membrane as it adsorbs on the membrane's surface, thus improving its resistance to lipid "domain" tearing. It can be hypothesized that propylene glycol, when incorporated to the membrane, introduces defects that absorb excessive pressure that could have caused lipid "domain" tearing, and glycerol, as another layer of coating on the bubble, further increases its resistance to tearing. FIG. 1 shows the formulation and in vitro as well as in vivo assessment of the new formulation, which includes both PG and Gly (PG/Gly. As controls, we also included bubbles, which have only PG (Pure PG) or Gly (Pure Gly) or lipids only (Pure PBS).

Materials a. C22 (DBPC)—(1,2-dibehenoyl-sn-glycero-3-phosphocholine)

b. DPPA—(1,2 Dipalmitoyl-sn-Glycero-3-Phosphate)

c. DPPE—(1,2-dipalmitoyl-sn-glycero-3-phosphoethanolamine)

d. DSPE-mPEG 2000—(1,2-distearoyl-snglycero-3-phosphoethanolamine-N-[methoxy(polyethylene glycol)-2000] (ammonium salt))

e. PBS—phosphate buffered saline f. Propylene glycol g. Glycerol

Preparation of Samples

PG/Gly (Product)

Sample was prepared by first dissolving the lipids (C22, DPPA, DPPE, and DPSE-mPEG 2000) in 0.5 mL propylene glycol at 80° C. Mixture of pre-heated glycerol and PBS was added and the resulting solution was sonicated for 10 mins. 1 mL of the solution was transferred to a 3 mL headspace vial, air was removed by a syringe, and air was replaced by injecting octafluoropropane ($C_3F_8$) gas.

Pure PG (Control 1)

Sample was prepared similar to PG/Gly but without any glycerol and using 1 mL of propylene glycol instead of 0.5 mL.

Pure Glycerol (Control 2)

Sample was prepared by first dissolving the lipids (C22, DPPA, DPPE, and DPSE-mPEG 2000) in 1 mL glycerol at 80° C. Preheated PBS was added then the resulting solution was sonicated for 10 mins. The rest is similar to PG/Gly.

Pure PBS (Control 3)

Sample was prepared by first dissolving the lipids (C22, DPPA, DPPE, and DPSE-mPEG 2000) in 5 mL PBS at 80° C. The rest is similar to PG/Gly.

Activation of Samples and Isolation of Nanobubbles

Solution was activated by mechanical shaking using a VialMix for 45 s. The activated solution was then centrifuged at 50 G for 5 mins to separate the nanobubbles from microbubbles. Nanobubble samples were taken at a fixed height from the base of the headspace vial.

Analysis of Size and Concentration of Nanobubbles

Methodology

The size and concentration of nanobubbles were analyzed using resonant mass measurement (Archimedes) equipped with a nanosensor. Nanobubbles were isolated and diluted with PBS. The diluted nanobubble solution was loaded to the instrument.

Results and Discussion

Figure 2A:
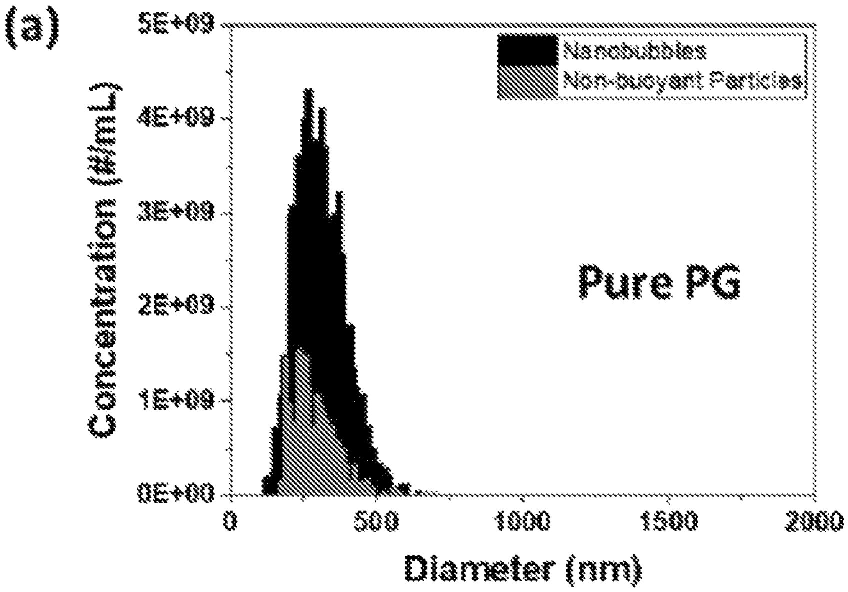
FIGS. 2(A-F) illustrate the analysis of size and concentration of nanobubbles and non-buoyant nanoparticles.
Figure 2B:
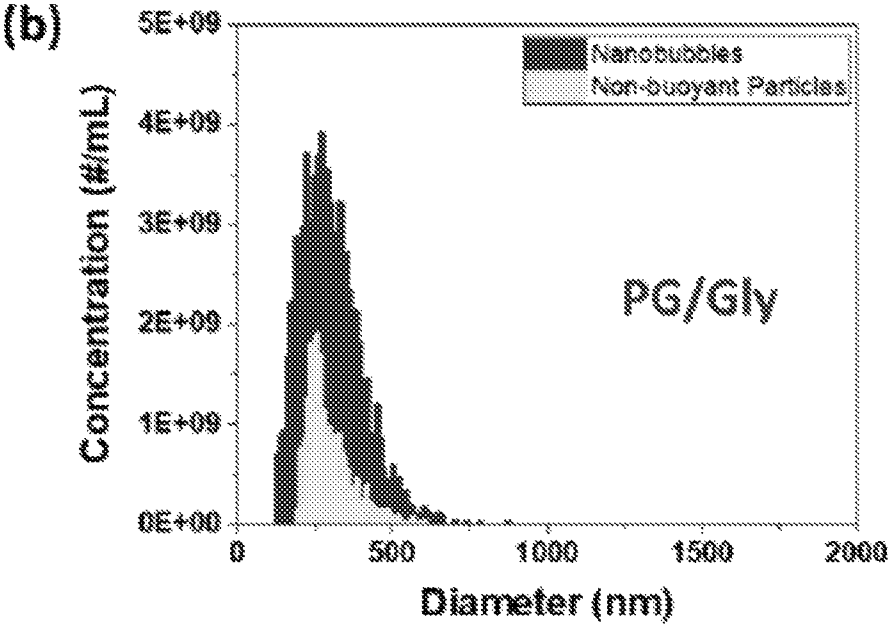
Figure 2C:
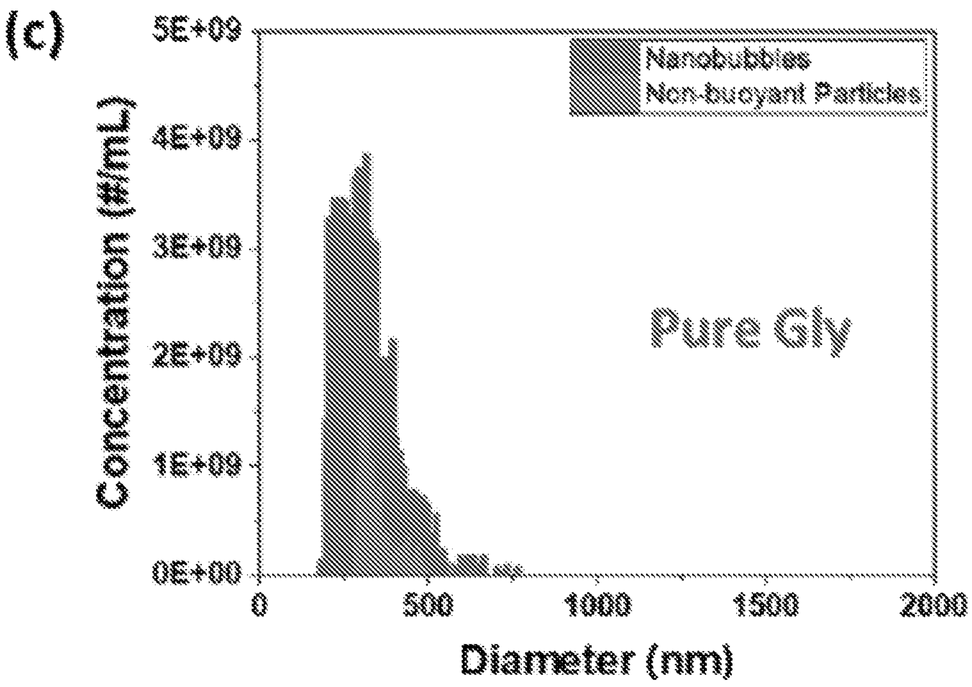
Figure 2D:
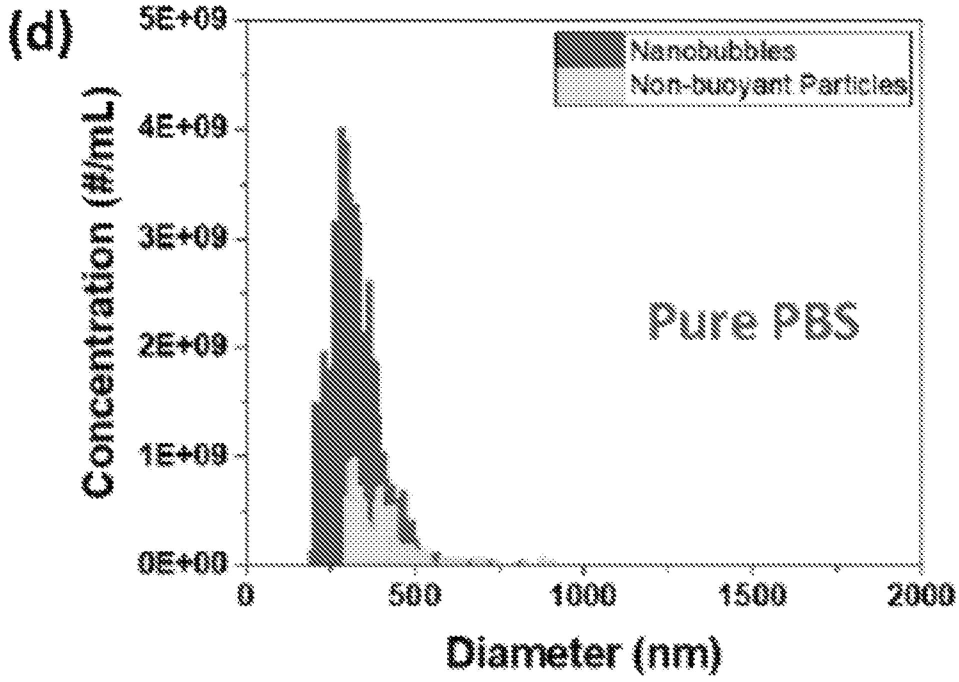
Figure 2E:
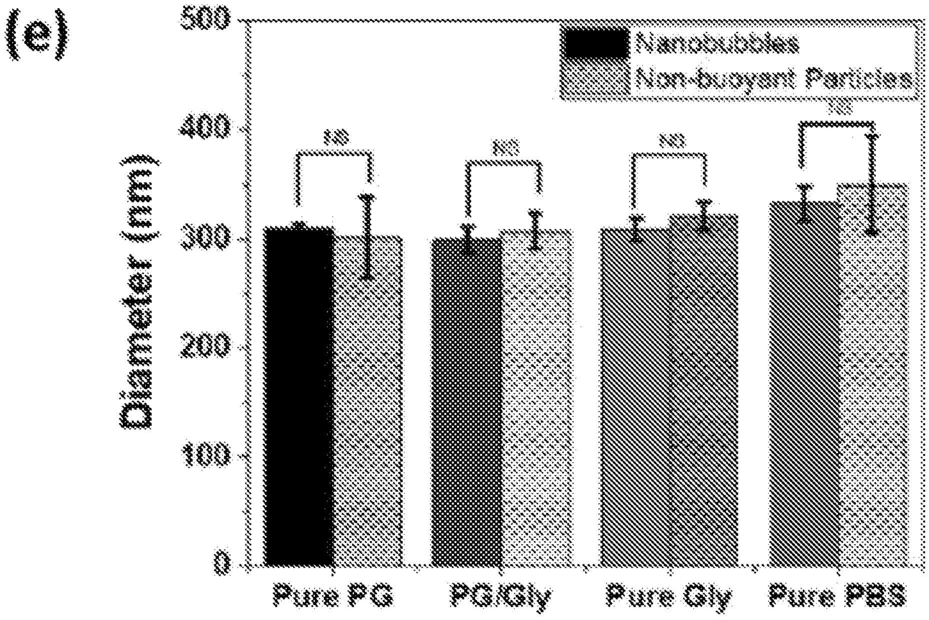
Figure 2F:
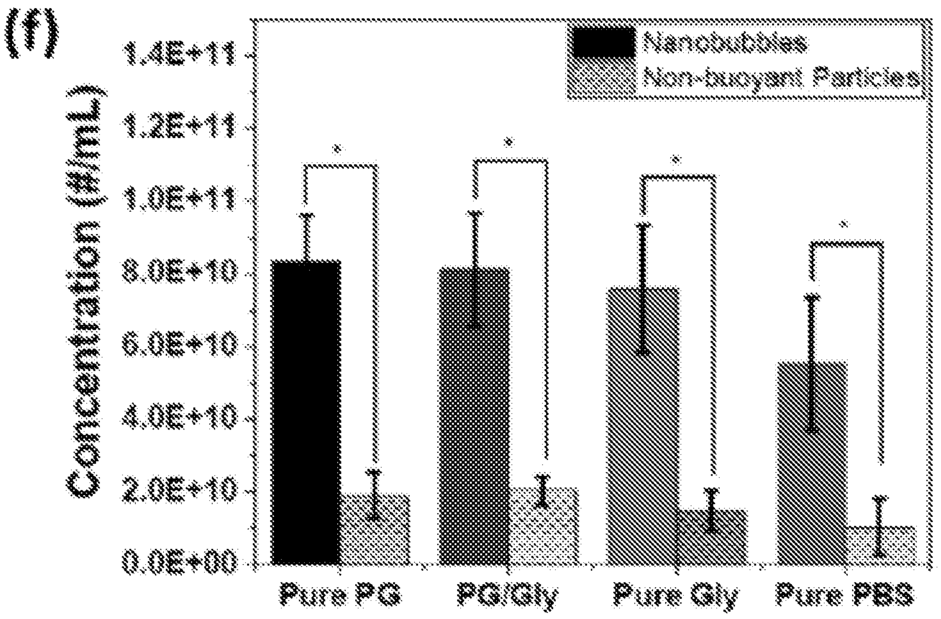

FIGS. 2A-D show the histogram of the nanobubbles and non-buoyant particles (liposomes and lipid chunks) for different formulations. It can be seen that there is nothing larger than 1 micron indicating that sample is purely composed of nanobubbles and nanosized non-buoyant particles. FIG. 2E shows that the average diameter of the nanobubbles and non-buoyant particles is around 300 nm and that there is no significant difference among the four samples. FIG. 2F shows the concentration of the nanobubbles and non-buoyant particles. No significant difference among the concentration of the nanobubbles and the concentration of the non-buoyant particles for the four samples can be observed. However, it can be seen that there is significantly more nanobubbles than non-buoyant particles for all samples.

Analysis of Charge of Nanobubbles

Methodology

Nanobubbles were isolated and diluted with PBS. The charge of the nanobubbles was determined using an Anton Paar Litesizer™ 500.

Results

Analysis of the surface charge (Table 1) of the nanobubbles and non-buoyant particles shows that all samples have negative charge but they are not significantly different among themselves.

TABLE 1

| Charge of Nanobubbles | |
|---|---|
| Sample | Zeta Potential (mV) |
| Pure PG | −2.53 ± 0.88 |
| PG/Gly | −2.15 ± 1.78 |
| Pure Glycerol | −2.04 ± 1.70 |

In Vitro Characterization (Initial Enhancement—Dependence of Frequency)

Methodology and Results

Nanobubbles are isolated and diluted with PBS. The ultrasound contrast is imaged by placing the diluted nanobubbles in a 1.5 wt % agarose phantom with a thick rectangular slit (made with a Lego piece mold) on a clinical ultrasound transducer. System acquisition parameters were set to contrast harmonic imaging (CHI) with varying harmonic frequency from 7-12.0 MHz, 0.1 mechanical index (MI), 65 dB dynamic range, and 70 dB gain.

Figure 3A:
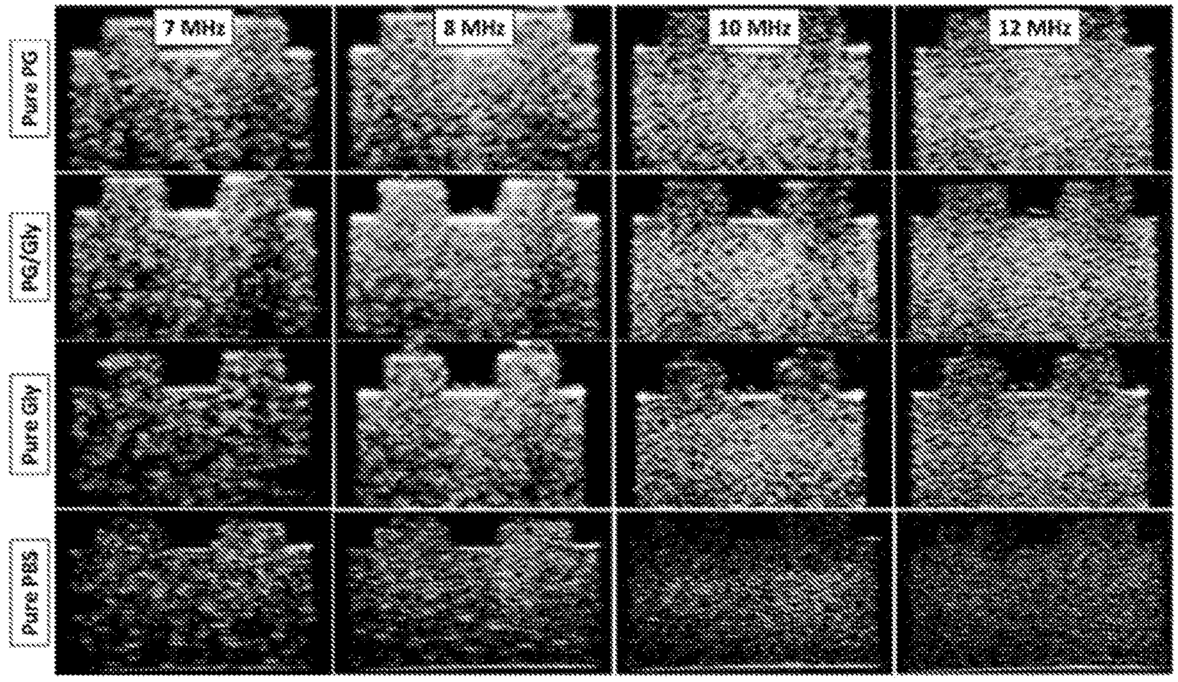
FIGS. 3(A-B) illustrate images and graph showing in vitro characterization (Initial enhancement—dependence on frequency) of PG, PG-Gly, and Gly nanobubbles (NBs).
Figure 3B:
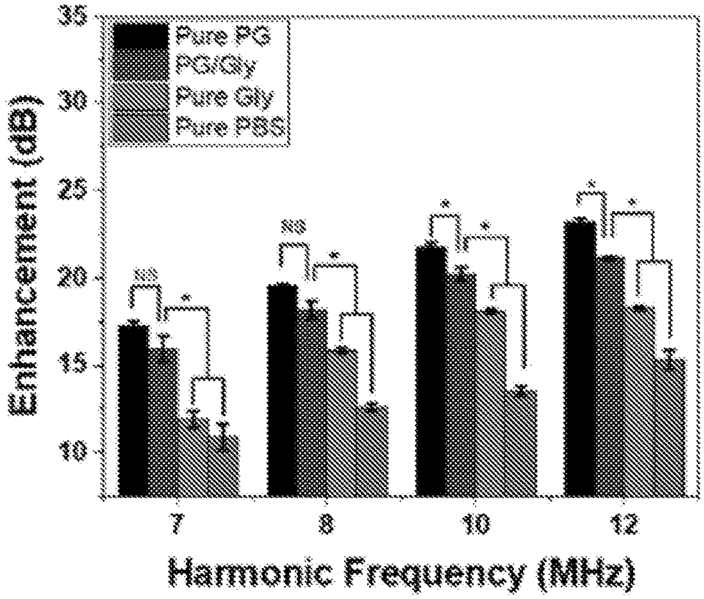

FIG. 3A shows the ultrasound images captured for four formulations and with varying harmonic frequency (7-12 MHz). It can be seen that the brightness (ultrasound intensity) and the resolution increase with increasing harmonic frequency. The difference in the ultrasound intensity with and without nanobubbles was calculated and reported as enhancement (dB). FIG. 3B shows the enhancement as a function of harmonic frequency. Pure PG and PG/Gly provide the highest enhancement when imaged at 7 and 8 MHz harmonic frequency. On the other hand, Pure PG provided the highest enhancement at 10 and 12 MHz. For all harmonic frequency, Pure PBS has the lowest enhancement among all the samples analyzed.

In Vitro Characterization (Initial Enhancement—Dependence on Peak Negative Pressure)

Nanobubbles are isolated and diluted with PBS. The ultrasound contrast is imaged by putting the diluted nanobubbles in a 1.5 wt % agarose phantom with a thick rectangular slit (made with a Lego piece mold) on a clinical ultrasound transducer. System acquisition parameters were set to contrast harmonic imaging (CHI) with 12.0 MHz harmonic frequency, with varying peak negative pressure (or mechanical index) from 245 to 465 kPa, 65 dB dynamic range, and 70 dB gain.

Figure 4A:
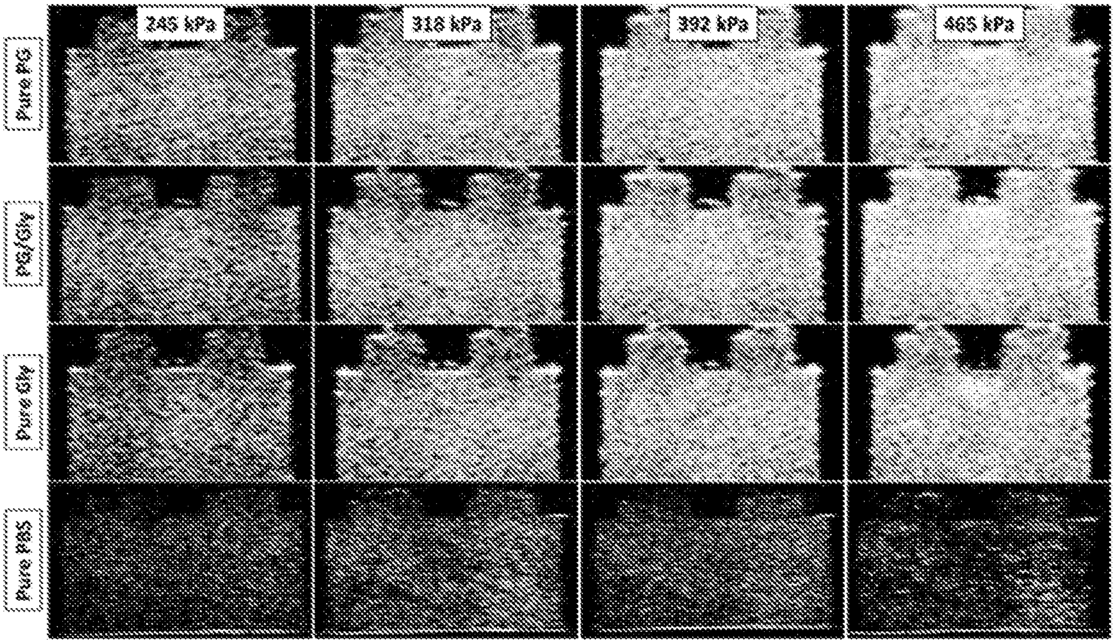
FIGS. 4(A-B) illustrate images and a graph showing in vitro Characterization (Initial enhancement—dependence on peak negative pressure) of PG, PG-Gly, and Gly nanobubbles (NBs).
Figure 4B:
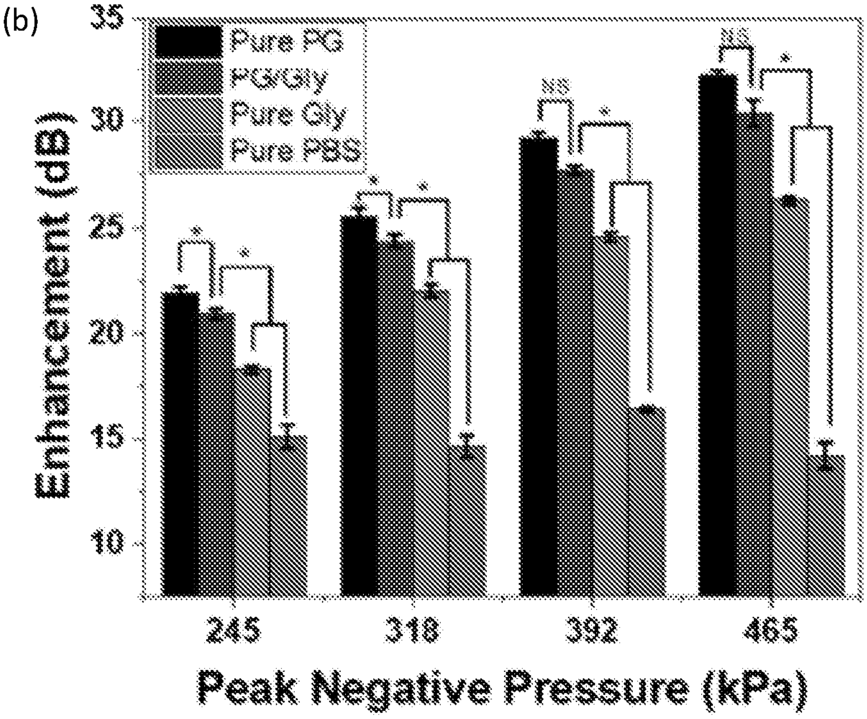

FIG. 4A shows the ultrasound images captured for the four samples and varying peak negative pressure. It can be seen that the brightness (ultrasound intensity) increases with increasing peak negative pressure. The difference in the ultrasound intensity with and without nanobubbles was calculated and reported as Enhancement (dB). FIG. 4B shows the enhancement as a function of peak negative pressure. It can be seen that Pure PG provides the highest enhancement when imaged at 245 and 318 kPa peak negative pressure. At higher peak negative pressure, Pure PG and PG/Gly provide the highest enhancement when imaged at 392 and 465 kPa peak negative pressure. For all peak negative pressures, Pure PBS provided the lowest enhancement among all the samples analyzed.

In Vitro Characterization (Stability—Signal Dissipation Over Time)

Figure 5A:
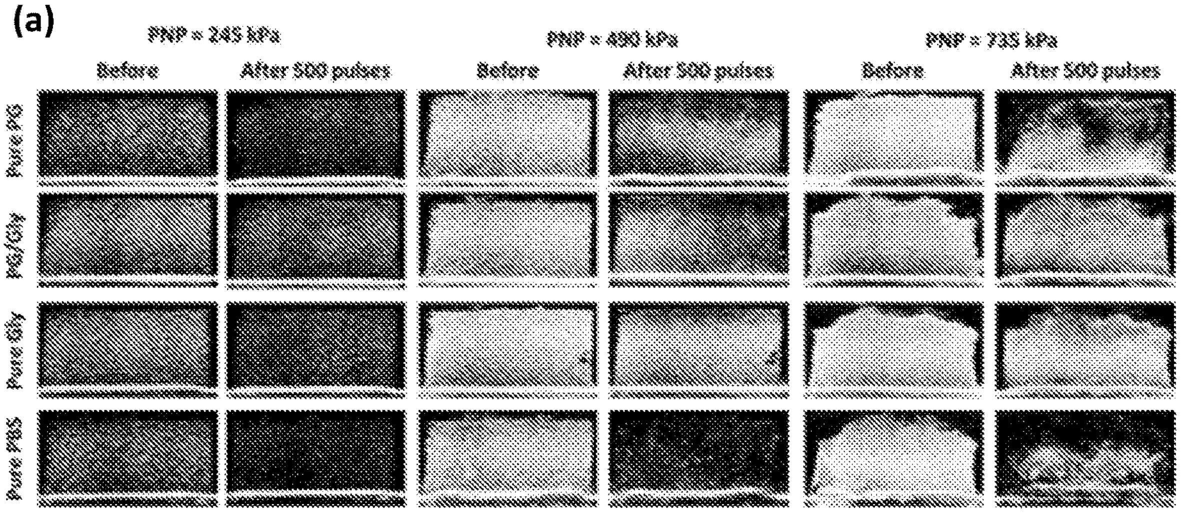
FIGS. 5(A-B) illustrate images and a graph showing in vitro characterization (Stability—signal dissipation over time) of PG, PG-Gly, and Gly nanobubbles (NBs).

Nanobubbles are isolated and diluted with PBS. The ultrasound contrast is imaged by putting the diluted nanobubbles in a 1.5 wt % agarose phantom with a thin rectangular slit on a clinical ultrasound transducer. System acquisition parameters were set to contrast harmonic imaging (CHI) with 12.0 MHz harmonic frequency, with varying peak negative pressure (or mechanical index) from 245 to 465 kPa, 65 dB dynamic range, 70 dB gain, and 15 frames per second (FIG. 5A). 500 frames of ultrasound images were gathered and the intensity per frame is analyzed with a built-in software (CHI-Q). In vitro half-life (in vitro $t_{1/2}$) was calculated by using the formula for first order decay.

Figure 5B:
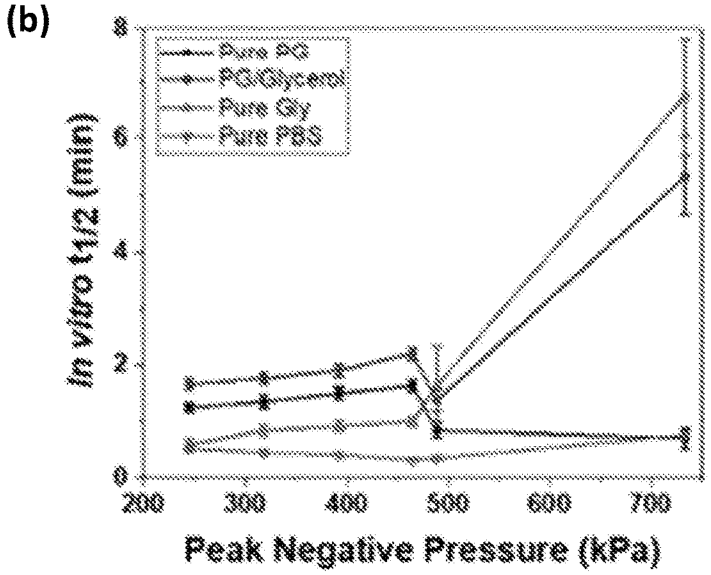

FIG. 5B shows the ultrasound images captured for the three samples before and after exposure to 500 ultrasound pulses with varying peak negative pressure (PNP). The brightness (ultrasound intensity) increases with increasing peak negative pressure. The difference in the ultrasound intensity with and without nanobubbles was calculated and reported as Enhancement (dB) and in vitro half-life (in vitro $t_{1/2}$) was calculated assuming first order decay. FIG. 5C shows the in vitro $t_{112}$ as a function of peak negative pressure. It can be seen that PG/Gly has the longest in vitro $t_{112}$ among all the samples for PNP less than 490 kPa. This implies that the nanobubbles made with combination of PG and glycerol are the most stable under ultrasound among all other formulations. Pure PG is the 2nd most stable, followed by Pure Gly, and lastly by Pure PBS. At PNP=490 kPa and 735 kPa, Pure Gly shows the highest stability followed closely by PG/Gly. This opens the door to potential mixed bubble imaging of different biomarkers and differential collapse of bubbles for new creative ultrasound applications.

In Vitro Characterization (Stability—Changes with Pulse Repetition Rate)

Nanobubbles are isolated and diluted with PBS. The ultrasound contrast is imaged by putting the diluted nanobubbles in a 1.5 wt % agarose phantom with a thin rectangular slit on a clinical ultrasound transducer. System acquisition parameters were set to contrast harmonic imaging (CHI) with 12.0 MHz harmonic frequency, with peak negative pressure of 245 kPa (or mechanical index of 0.1), 65 dB dynamic range, 70 dB gain, and varying number of ultrasound pulses per second (1 to 15). 500 frames of ultrasound images were gathered and the intensity per frame is analyzed with a built-in software (CHI-Q). In vitro half-life (in vitro $t_{1/2}$) was calculated by using the formula for first order decay.

Figure 6:
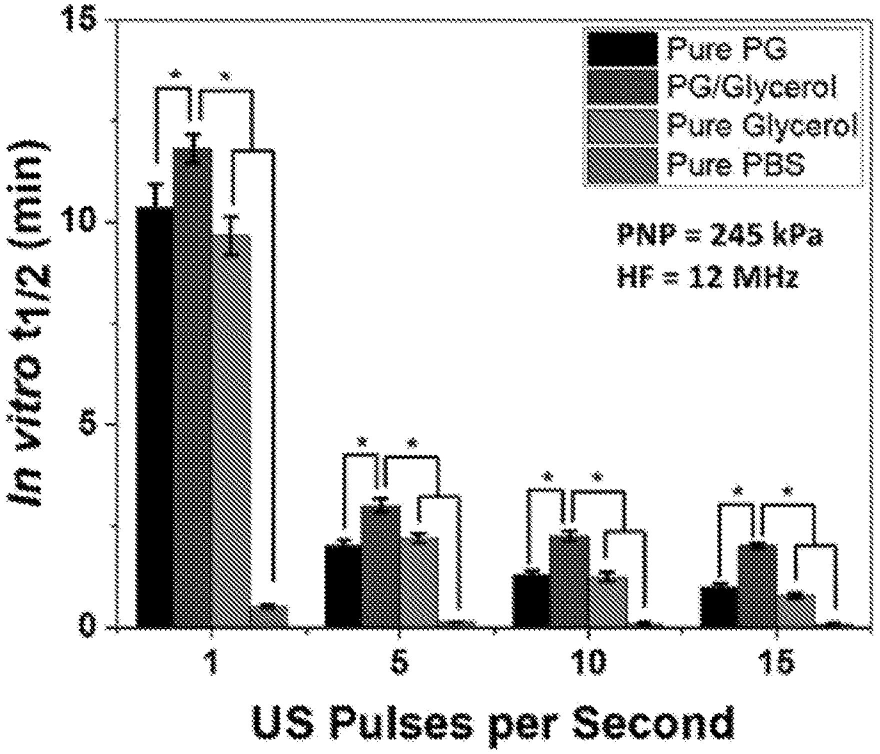
FIG. 6 illustrates images and a graph showing in vitro characterization (Stability—changes with pulse repetition) PG, PG-Gly, and Gly nanobubbles (NBs).

The difference in the ultrasound intensity with and without nanobubbles was calculated and reported as Enhancement (dB) and in vitro half-life (in vitro $t_{1/2}$) was calculated assuming first order decay. FIG. 6 shows the in vitro $t_{1/2}$ as a function of number of US pulses per second. It can be seen that PG/Gly has the longest in vitro tin, among all the samples regardless of the number of US pulses per second. This implies that the nanobubbles made with combination of PG and glycerol is the most stable under ultrasound among all other formulations. Pure PG is the 2nd most stable, followed by Pure Gly, and lastly Pure PBS.

In Vivo Characterization (Kidney, n=3)

Figure 7A:
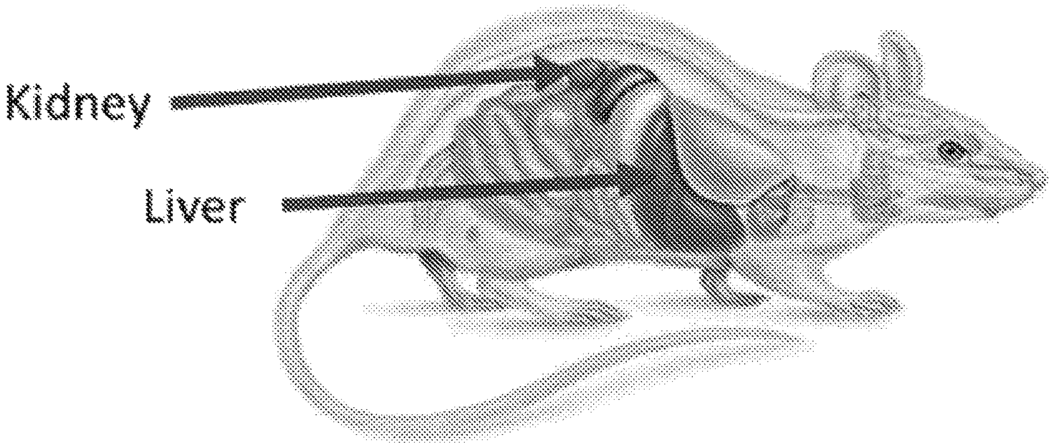
FIGS. 7(A-F) illustrate in vivo characterization of PG, PG-Gly, and Gly nanobubbles (NBs) in mouse kidney stability relative to commercially available UCA in mice. (A) PG, PG-Gly, and Gly NBs and commercially available ultrasound contrast agent (UCA) (Lumason) were injected via tail-vein and a cross-section of the kidney was imaged at 12 MHz, 245 kPa pressure, and 0.2 frames per second. (B) Left: Representative B-mode images of the kidney and liver before the injection of UCAs. 0 min-20 mins: Series of images showing the signal onset and signal decay of various UCAs at different time points. (C) Average signal decay curve of NBs and Lumason® showing the delayed signal decay onset and longer in vivo half-life of PG-Gly-PL. (D), In vivo maximum enhancement, (E), in vivo washout half-life, and (F), in vivo decay onset of NBs and Lumason extracted from the enhancement vs. time curve.

200 μL of nanobubbles are isolated and injected via mouse's tail vein. The ultrasound transducer was oriented in such a way that both kidney and liver can be imaged at the same time (FIG. 7A). After injection of nanobubbles, the change of tissue contrast of the kidney was measured using contrast harmonic imaging (CHI, frequency 12 MHz; peak negative pressure of 245 kPa or MI of 0.10; dynamic range, 65 dB; gain, 80 dB; imaging frame rate, 0.2 frame/s). Ultrasound raw data were continuously acquired for 30 mins and the intensity per frame is analyzed with a built-in software (CHI-Q). For comparison, commercially-available ultrasound contrast agent (Lumason, microbubble) was also analyzed. Lumason was diluted in such a way that it has the same injected gas volume as the other samples. The time-enhancement curve for Lumason was analyzed by fitting a lognormal function, whereas the time-enhancement curve for the other samples was analyzed by fitting a four parameter logistic function.

Figure 7B:
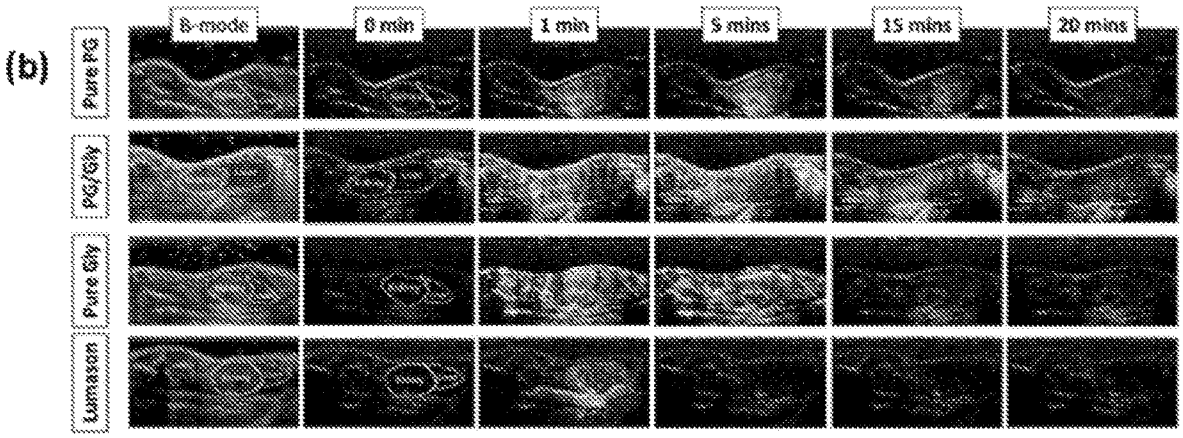
Figure 7C:
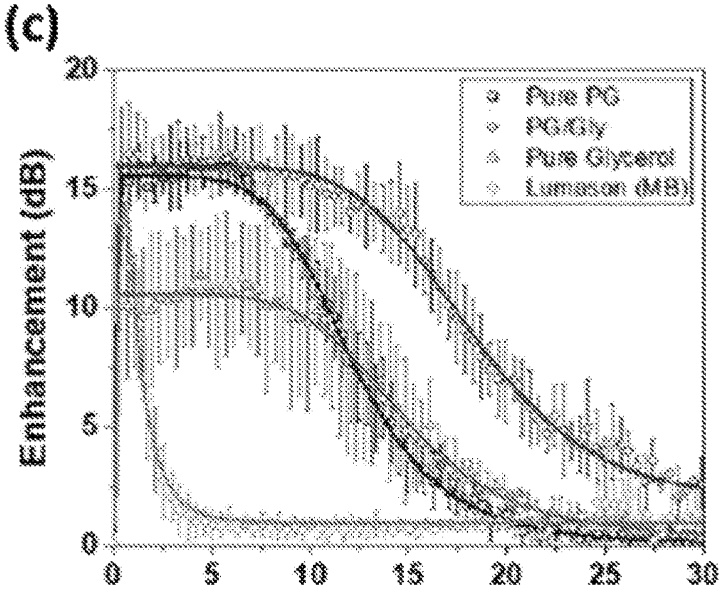
Figure 7D:
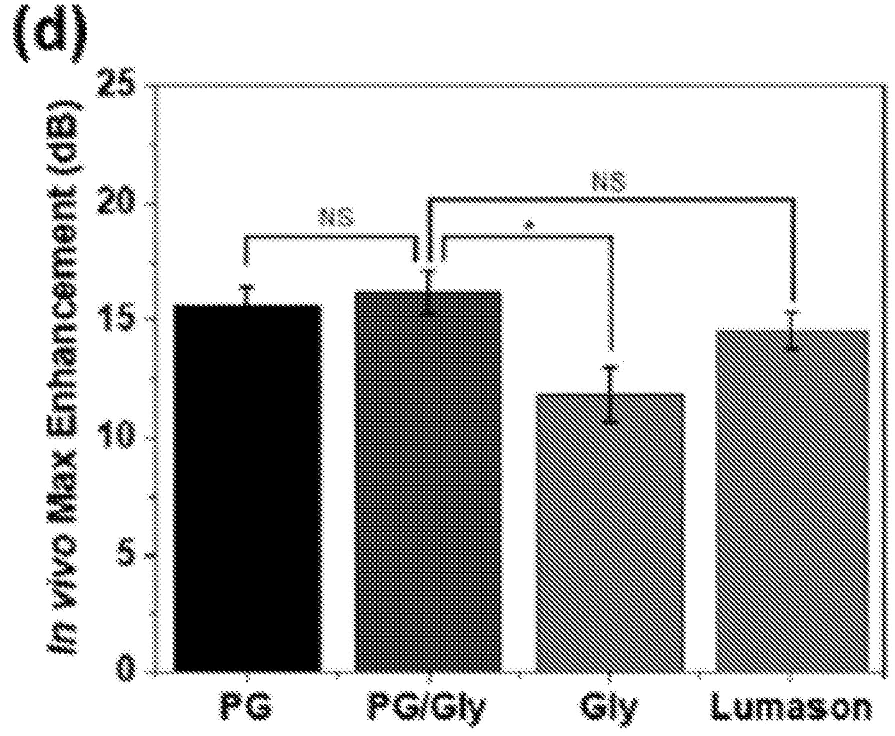
Figure 7E:
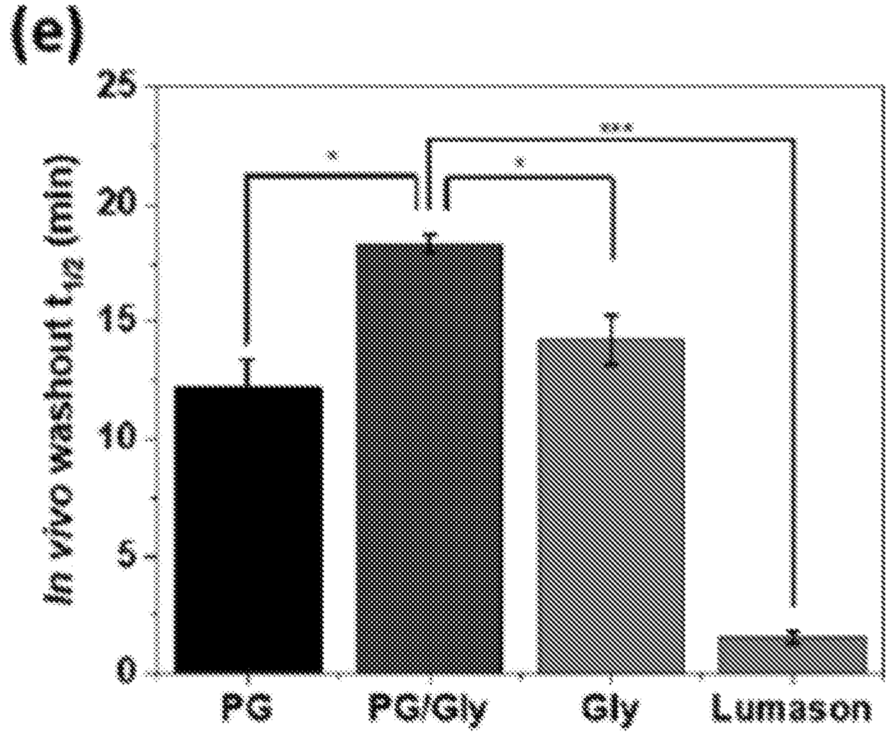
Figure 7F:
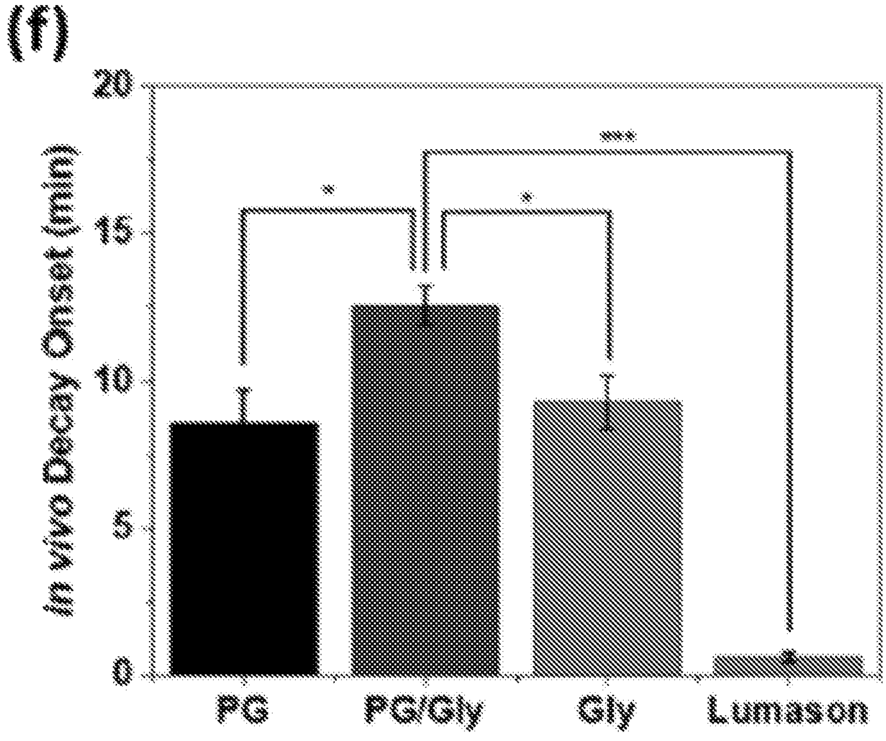

FIG. 7B shows that ultrasound images of mouse before and after the injection of nanobubbles or Lumason. All samples show improvement in the contrast of kidney 1 min after injection but the signal from Lumason disappears after 5 min Pure Gly improves the contrast for at least 5 mins, Pure PG for at least 15 mins, and PG/Gly for at least 20 mins. The difference in the ultrasound intensity with and without contrast agent was calculated and reported as Enhancement (dB). The time-enhancement curves are plotted in FIG. 7C. Lumason follows a lognormal behavior that is typical for clinical ultrasound contrast agents while, the nanobubbles follow a logistic behavior wherein the intensity remains at its maximum for some time before it starts to decay. Analysis of the in vivo maximum enhancement (FIG. 7D) shows that there is no significant difference among Pure PG, PG/Gly, and Lumason. Analysis of the in vivo washout half-life (in vivo washout $t_{1/2}$) of the different samples as shown in FIG. 7E indicates that the PG/Gly is the most stable with in vivo half-life 11.7× longer than Lumason's. As mentioned earlier, the ultrasound contrast enhancement for nanobubbles remained at its maximum for some time before it starts to decay. It is therefore important to compare the time at which the signal starts to decay, herein refer to as in vivo onset decay. As shown in FIG. 7F, the in vivo signal decay onset of PG/Gly is significantly higher than the other samples' and it is 19.5× longer as compared to Lumason's.

In Vivo Characterization (Liver, n=3)

200 uL of nanobubbles are isolated and injected via mouse's tail vein. The ultrasound transducer was oriented in such a way that both kidney and liver can be imaged at the same time (FIG. 7A). After injection of nanobubbles, the change of tissue contrast of the kidney was measured using contrast harmonic imaging (CHI, frequency 12 MHz; peak negative pressure of 245 kPa or MI of 0.10; dynamic range, 65 dB; gain, 80 dB; imaging frame rate, 0.2 frame/s). Ultrasound raw data were continuously acquired for 30 mins and the intensity per frame is analyzed with the built-in software (CHI-Q). For comparison, commercially-available ultrasound contrast agent (Lumason, microbubble) was also analyzed. Lumason was diluted in such a way that it has the same injected gas volume as the other samples. The time-enhancement curve for Lumason was analyzed by fitting a lognormal function, whereas the time-enhancement curve for the other samples was analyzed by fitting a four parameter logistic function.

Figure 8A:
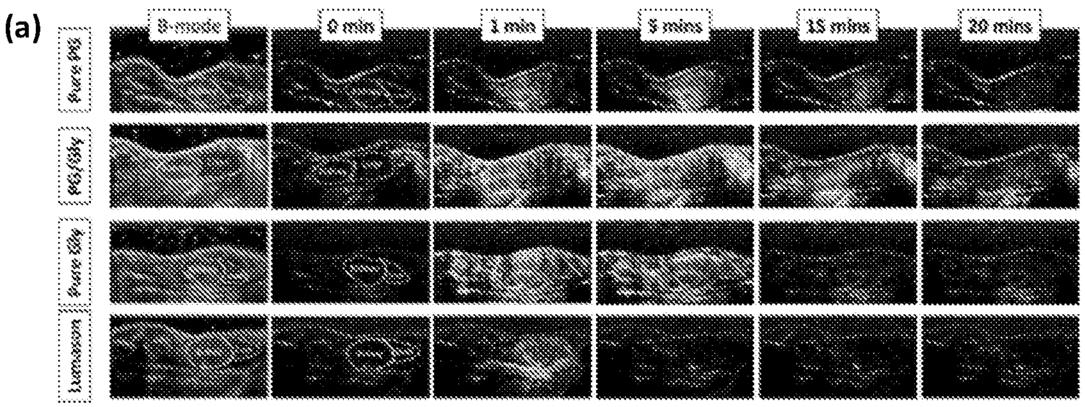
FIGS. 8(A-E) illustrate in vivo characterization of PG, PG-Gly, and Gly nanobubbles (NBs) in mouse liver stability relative to commercially available UCA in mice. PG, PG-Gly, and Gly NBs and commercially available UCA (Lumason) were injected via tail-vein and a cross-section of the kidney and liver was imaged at 12 MHz, 245 kPa pressure, and 0.2 frames per second. (A) Left: Representative B-mode images of the kidney and liver before the injection of UCAs. 0 min-20 mins: Series of images showing the signal onset and signal decay of various UCAs at different time points. (B), Representative signal decay curve of NBs and Lumason® showing the delayed signal decay onset and longer in vivo half-life of PG-Gly-PL. (C), In vivo maximum enhancement, (D) in vivo washout half-life, and (E), in vivo decay onset of NBs and Lumason extracted from the enhancement vs. time curve FIGS. 9(A-C) illustrate X-ray diffraction of the nanobubbles membrane and its components.
Figure 8B:
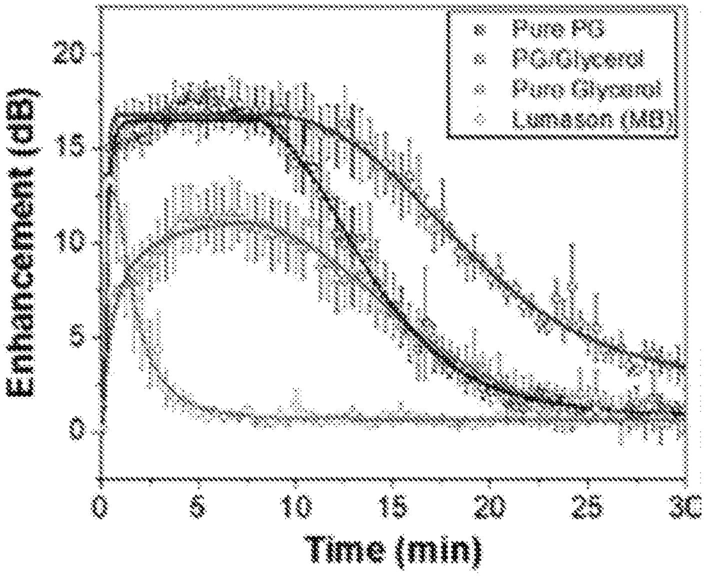
Figure 8C:
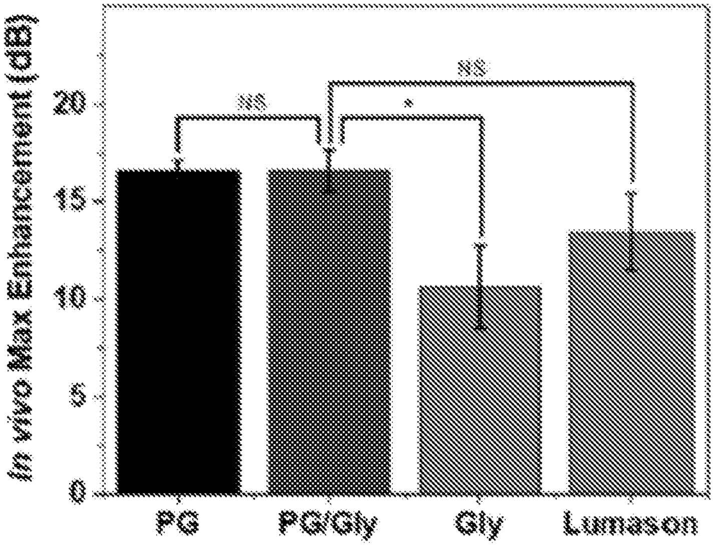
Figure 8D:
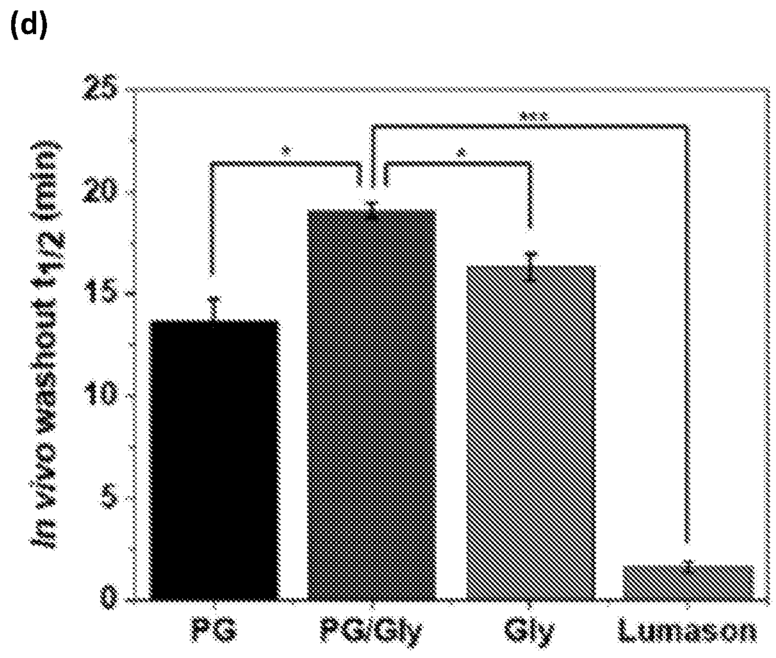
Figure 8E:
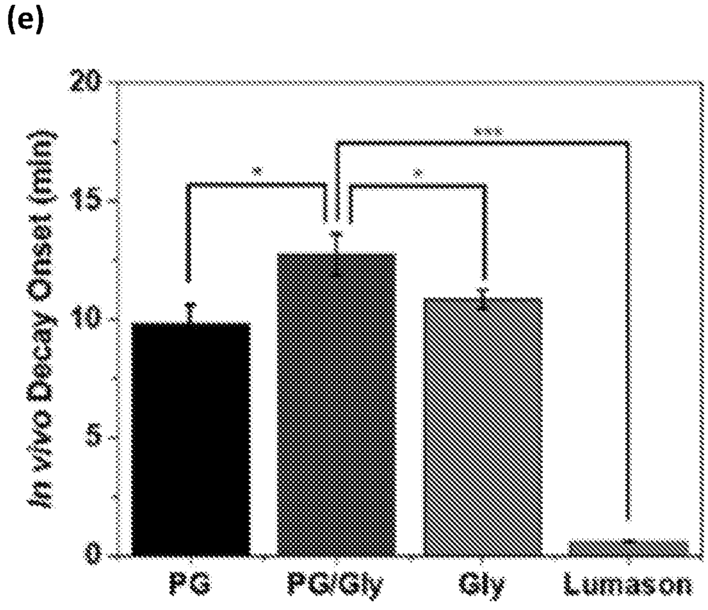

FIG. 8A shows that ultrasound images of mouse before and after the injection of nanobubbles or Lumason. All samples show improvement in the contrast of liver 1 min after injection but the signal from Lumason disappears after 5 min Pure Gly improves the contrast for at least 5 mins, Pure PG for at least 15 mins, and PG/Gly for at least 20 mins. The difference in the ultrasound intensity with and without contrast agent was calculated and reported as Enhancement (dB). The time-enhancement curves are plotted in FIG. 8B. It can be seen that Lumason follows a lognormal behavior that is typical for clinical ultrasound contrast agents. On the other hand, the nanobubbles follow a logistic behavior wherein the intensity remains at its maximum for some time before it starts to decay. Analysis of the in vivo maximum enhancement (FIG. 8C) shows that there is no significant difference among Pure PG, PG/Gly, and Lumason. Analysis of the in vivo half-life of the different samples as shown in FIG. 8E indicates that the PG/Gly is the most stable with in vivo half-life that is 11.7× longer than Lumason's. As mentioned earlier, the ultrasound contrast enhancement for nanobubbles remained at its maximum for some time before it starts to decay. It is therefore important the time at which the signal starts to decay, or the in vivo signal decay onset. As shown in FIG. 8F, the in vivo signal decay onset of PG/Gly is significantly higher than the other samples' and is 20.2× longer than Lumason's.

X-Ray Diffraction of the Nanobubble Membrane

Nanobubble solution was isolated and freeze-dried overnight removing the water and $C_3F_8$ and leaving the membrane of the nanobubbles. The nanobubbles membrane was analyzed using X-ray diffraction (XRD) to determine its crystallinity. The distance between the membrane components was calculated using Bragg's equation.

Figure 9A:
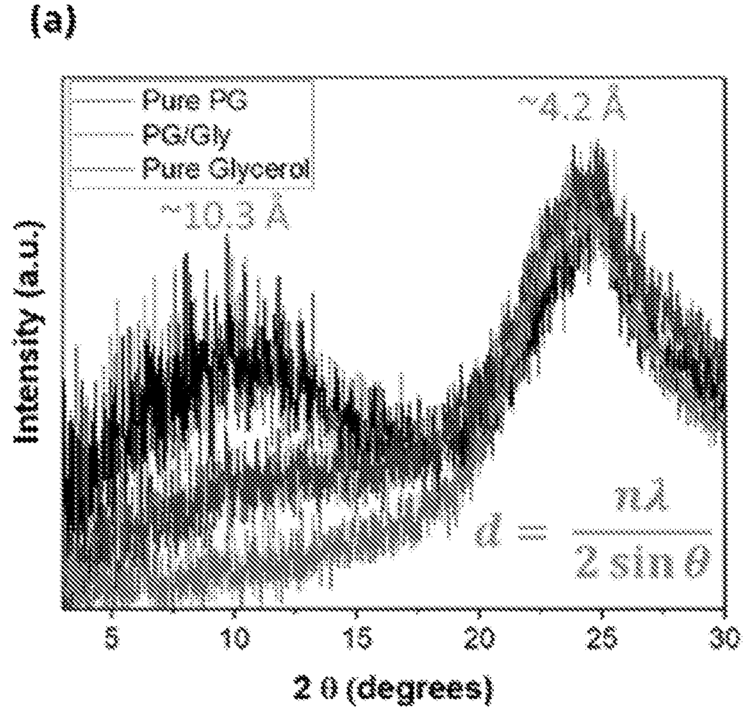
Figure 9B:
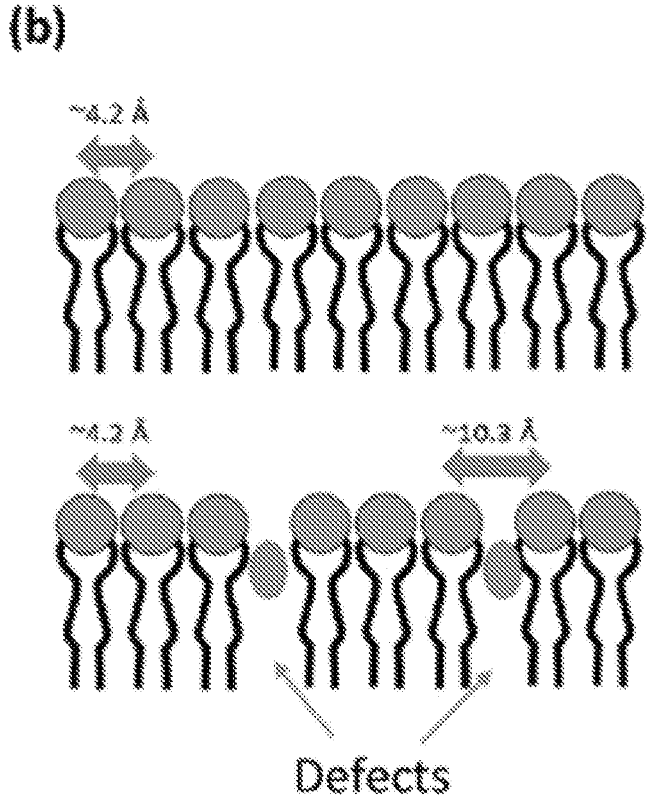
Figure 9C:
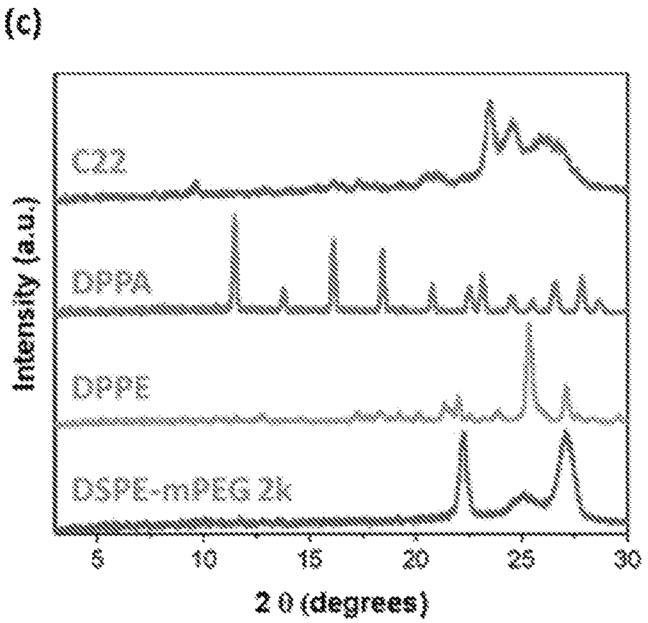

The XRD spectra of the nanobubble membrane for different formulations are shown in FIG. 9A. Nanobubble made with Pure Gly shows a peak centered at 2θ=~25° which corresponds to a distance, d=~4.5 Å. This is the distance between the phospholipid components in the nanobubble membrane and this value is consistent with what has been reported before. Nanobubbles made with Pure PG shows another broad peak centered at 2θ=~10° which corresponds to a distance, d=~10.3 Å. This implies that the addition of PG causes some regions in the nanobubble membrane to have components farther away from each other, i.e. introducing defects on the membrane. The schematic on the increase in the distance between the components of the membrane is shown in FIG. 9B. For Pure Gly we can see that the phospholipids are separated by ~4.5 Å distance, but with Pure PG there are regions with d=~4.5 Å and other regions with d=~10.3 Å. PG/Gly also has a small broad peak at 2θ=~10.3° implying that it also has regions with d=~10.3 Å separation but not as many as with Pure PG. XRD spectra of the pure components shown in FIG. 9C do not show the broad peak at 2θ=~10.3° implying that the presence of that peak is caused by PG.

Surface Tension Measurement

The surface tension of the liposome solution (solution before activation) was measured by three different techniques: (a) pendant drop, (b) rising bubble with air, and (c) rising bubble with $C_3F_8$. For the pendant drop, a picture of a droplet of the liposome solution suspended at the tip of a syringe was taken. The image was analyzed by a commercial software to calculate for the surface tension based on the shape of the droplet. For the rising bubble, a picture of bubble containing either air or $C_3F_8$ in the liposome solution was taken and the image was analyzed by a commercial software to calculate the surface tension based on the shape of the bubble.

Figure 10A:
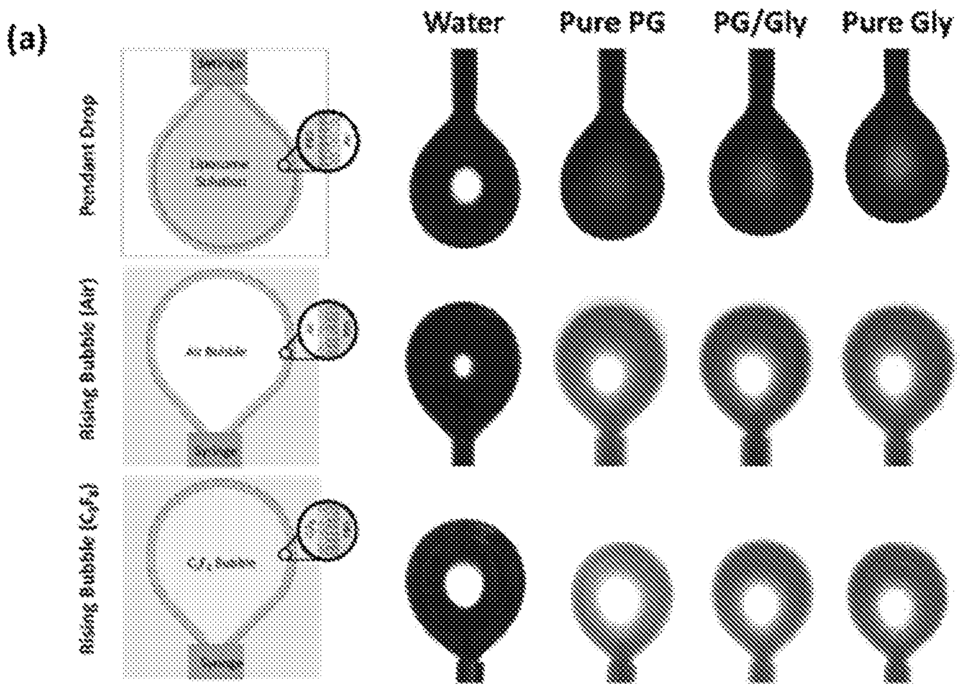
FIGS. 10(A-B) illustrate surface tension measurement.
Figure 10B:
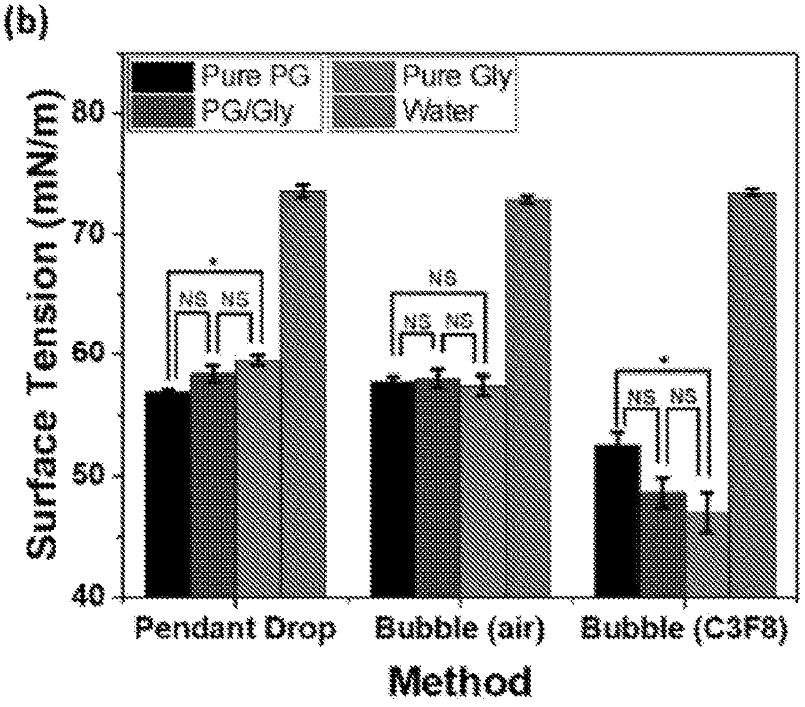

FIG. 10A shows the images of the droplets or bubbles used for determination of surface tension. The measured surface tension is shown in FIG. 10B. The surface tension of water is measured to be constant at ~72 mN/m regardless of the technique. There is a significant difference on the surface tension between Pure PG and Pure Gly when measured via pendant drop or rising bubble ($C_3F_8$). The surface tension of PG/Gly is always similar to that of Pure PG or Pure Gly regardless of the measurement technique.

Figure 11A:
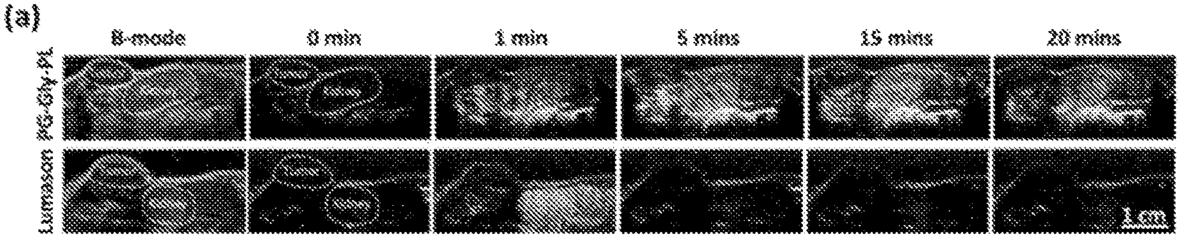
FIGS. 11(A-C) illustrate in vivo characterization of NBs in mouse kidney and flank colorectal tumor stability relative to commercially available UCA (Lumason) in mice. A, NBs or Lumason were injected via tail-vein and a cross-section of the kidney and flank tumor was imaged at 12 MHz, 245 kPa pressure, and 0.2 frames per second. Left: Representative B-mode images of the kidney and tumor before the injection of UCAs. 0 min-20 mins: Series of images showing the signal onset and signal decay of various UCAs at different time points. Minimal to no contrast can be observed before injection (t=0) which is expected because backscatter signals from kidney and tumor do not have any nonlinear properties. B-C, Representative signal decay curves of PG-Gly-PL and Lumason® showing the delayed signal decay onset and longer in vivo half-life of PG-Gly-PL.
Figure 11B:
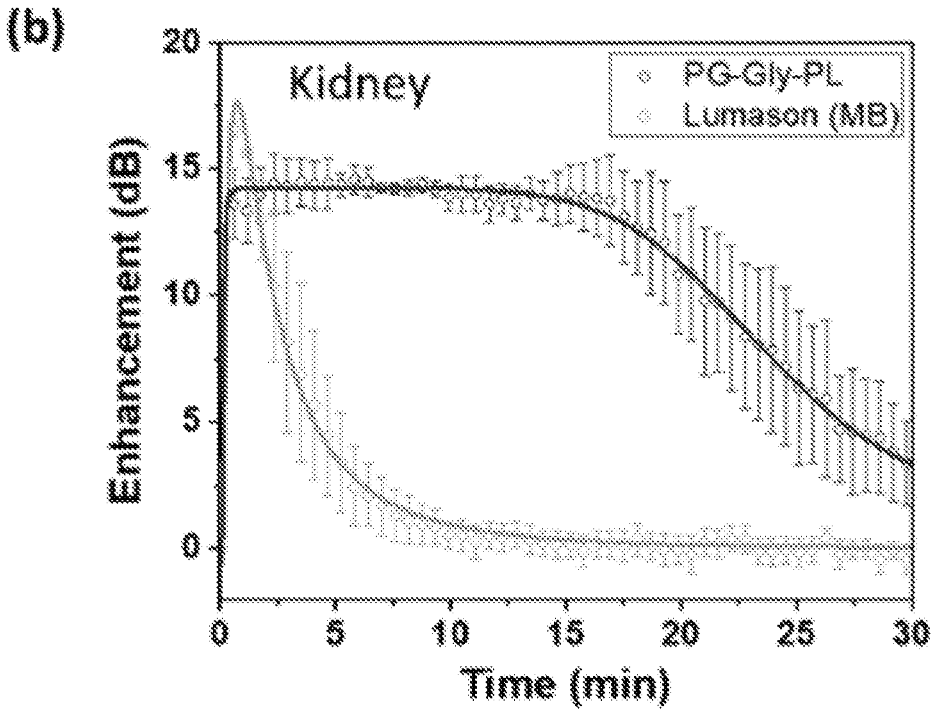
Figure 11C:
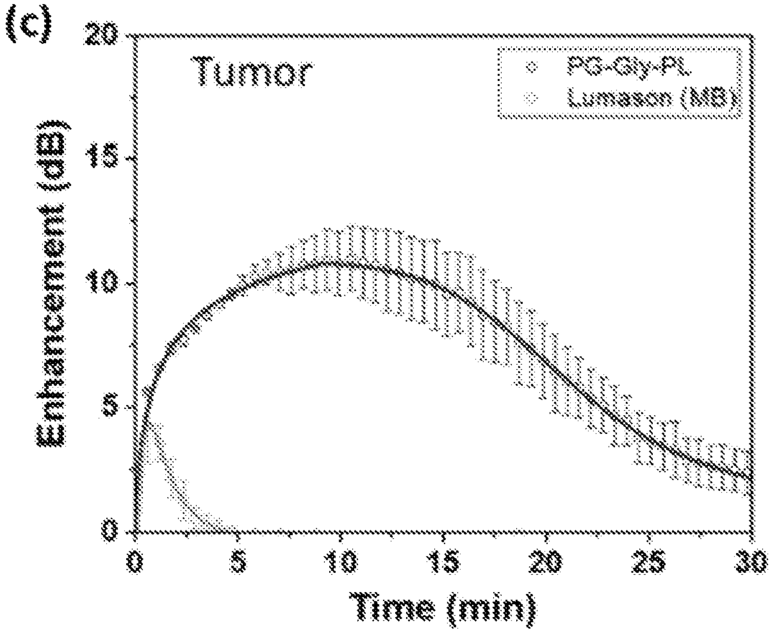
Figure 12A:
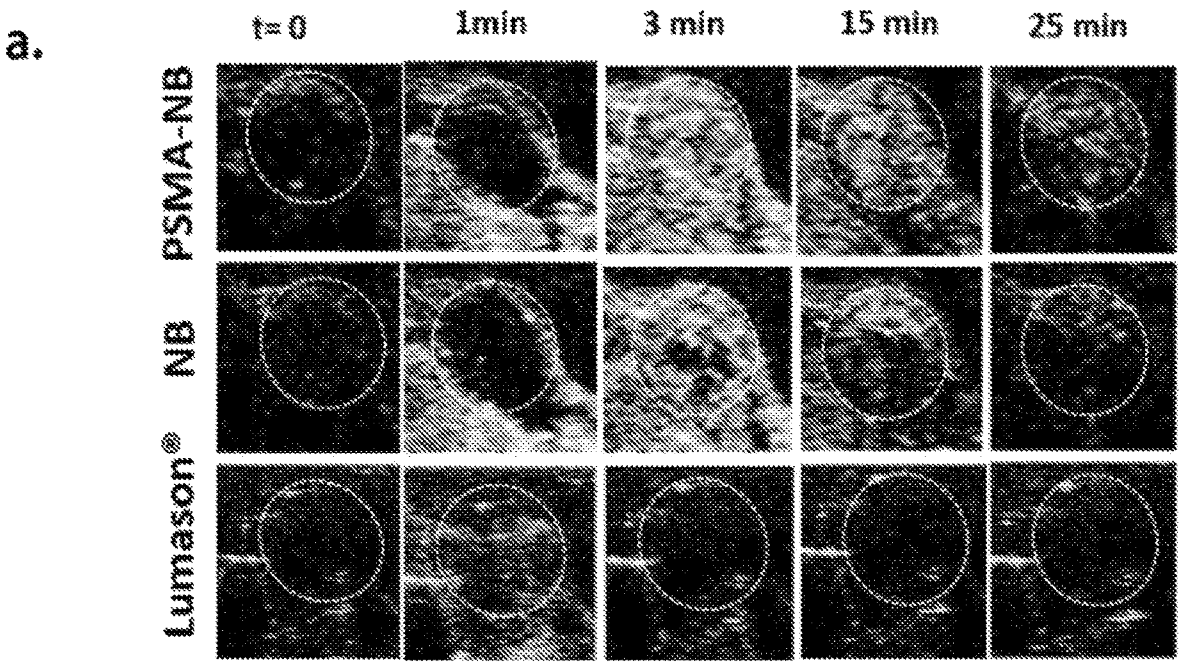
FIGS. 12(A-D) illustrate (A) Representative US-imaging results of the targeted PSMA-NB, NB and Lumason in PC3pip tumor (B) The signal enhancement of the PC3pip after IV administration of contrast agents (C) US signal obtained from PSMA-NB or NB normalized to the same bubble signal in kidney at each time point (n=7). D) experimental scheme for NB extravasation study and the US signal intensities at peak, t=25 min, after perfusion and after flash.
Figure 12B:
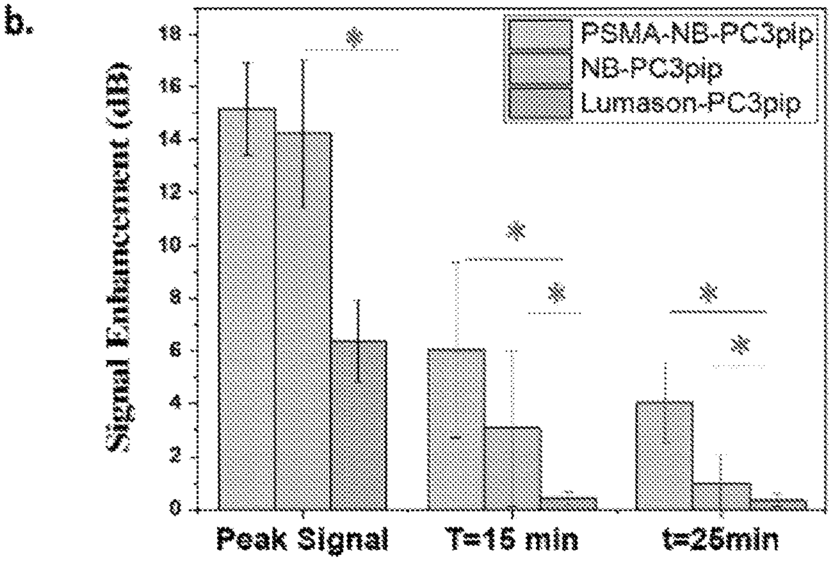
Figure 12C:
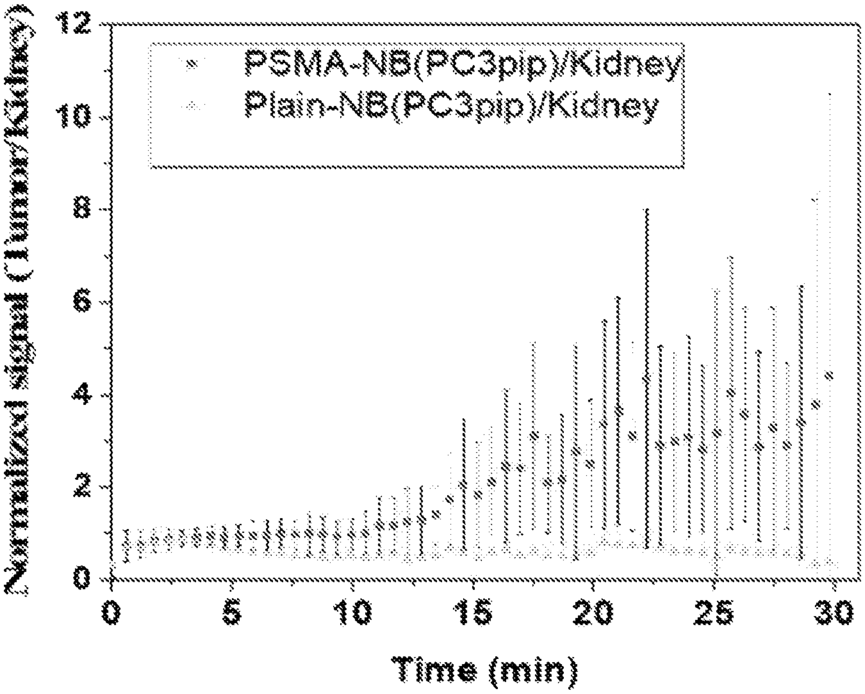
Figure 12D:
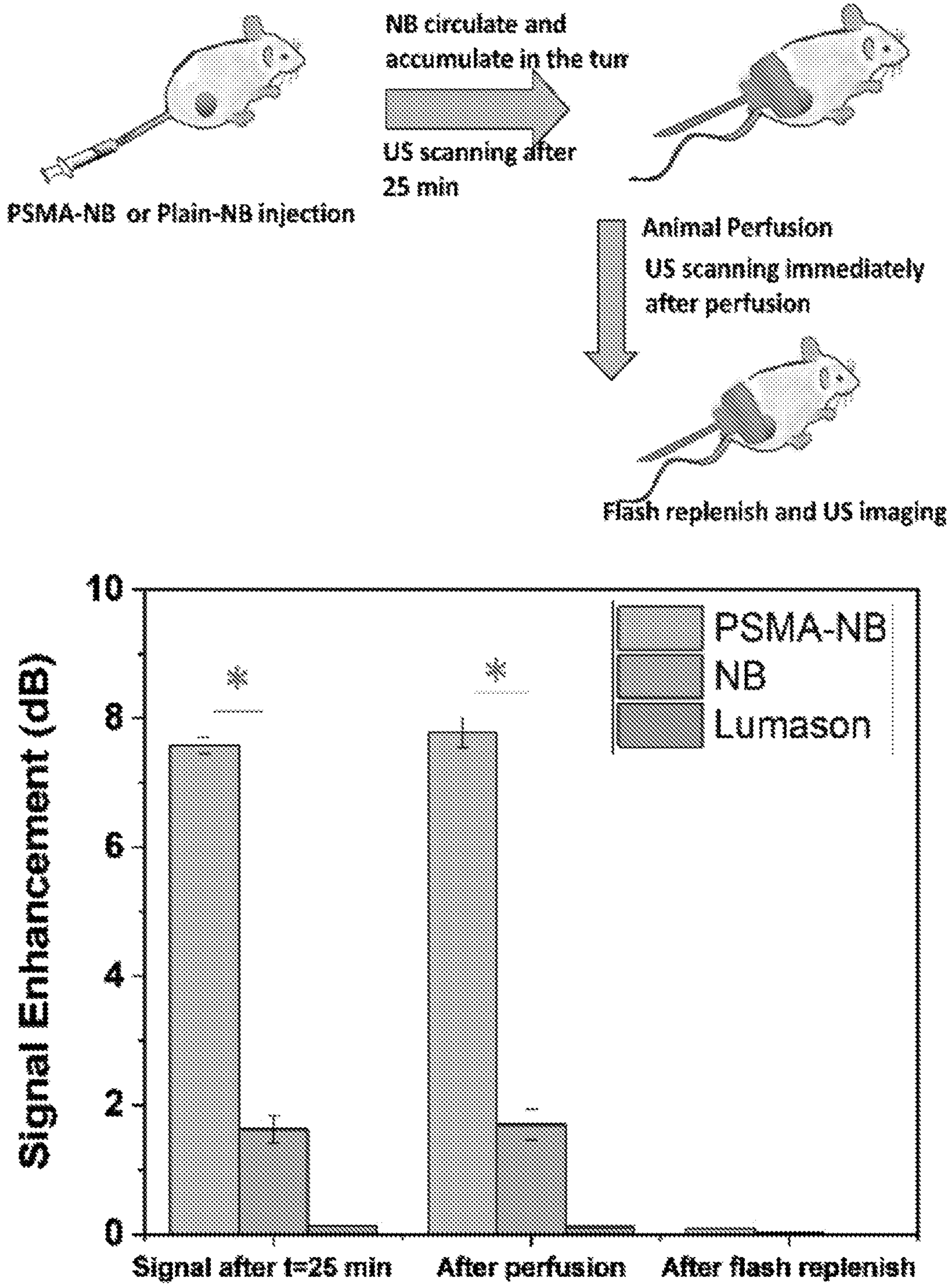

We have formulated ultrasound contrast agents visible with clinically available nonlinear (contrast) ultrasound imaging sequences at frequencies of 3-18 MHz which are on an order of magnitude smaller in diameter (~300 nm vs. ~3000 nm for commercial MBs) and 12-20 fold more stable (in terms of in vivo circulation time) than commercially available entities. FIG. 11 below shows nanobubbles in action in the kidney.

Figure 13A:
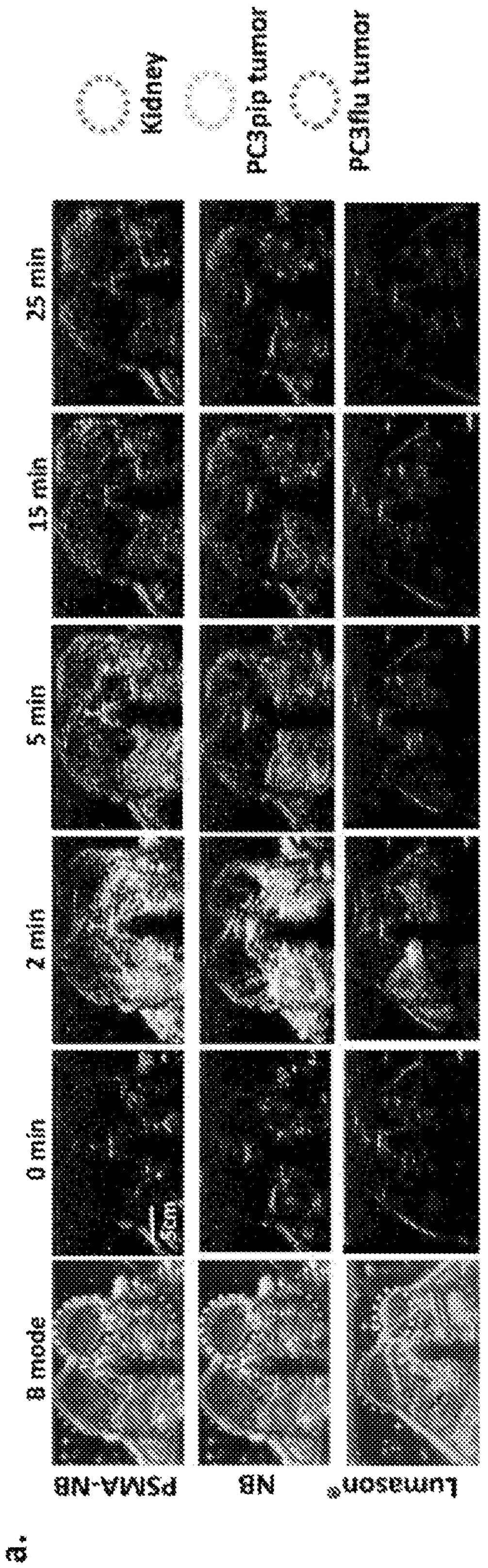
FIGS. 13(A-B) illustrate PSMA-NB enabled imaging of prolonged enhanced US signal in PSMA-positive PC3pip tumors. (A) Representative US imaging results of the targeted PSMA-NB, NB and Lumason® in PC3pip tumor, PC3flu tumor and kidneys. Bubbles were administered via tail vein and both PC3pip and PC3flu tumors and kidneys were imaged at 12 MHz, 245 kPa pressure, and 0.2 frames per second for 30 min Left two columns show the B-mode and contrast harmonic imaging (CHI) mode images of tumors and kidneys before injection. The series of images shows the CHI images at different time point after bubble administration. At the peak intensity, the contrast in both PC3pip and PC3flu tumors was similar with both NB and PSMA-NB. At later time points PC3pip tumor show high contrast with PSMA-NB. (B) Mean time intensity curves (TIC) of PC3pip tumors, PC3flu tumors, and kidneys after IV bubble administration. The TIC data was collected from uniform regions of interest drawn on the acquired image stacks.
Figure 13B:
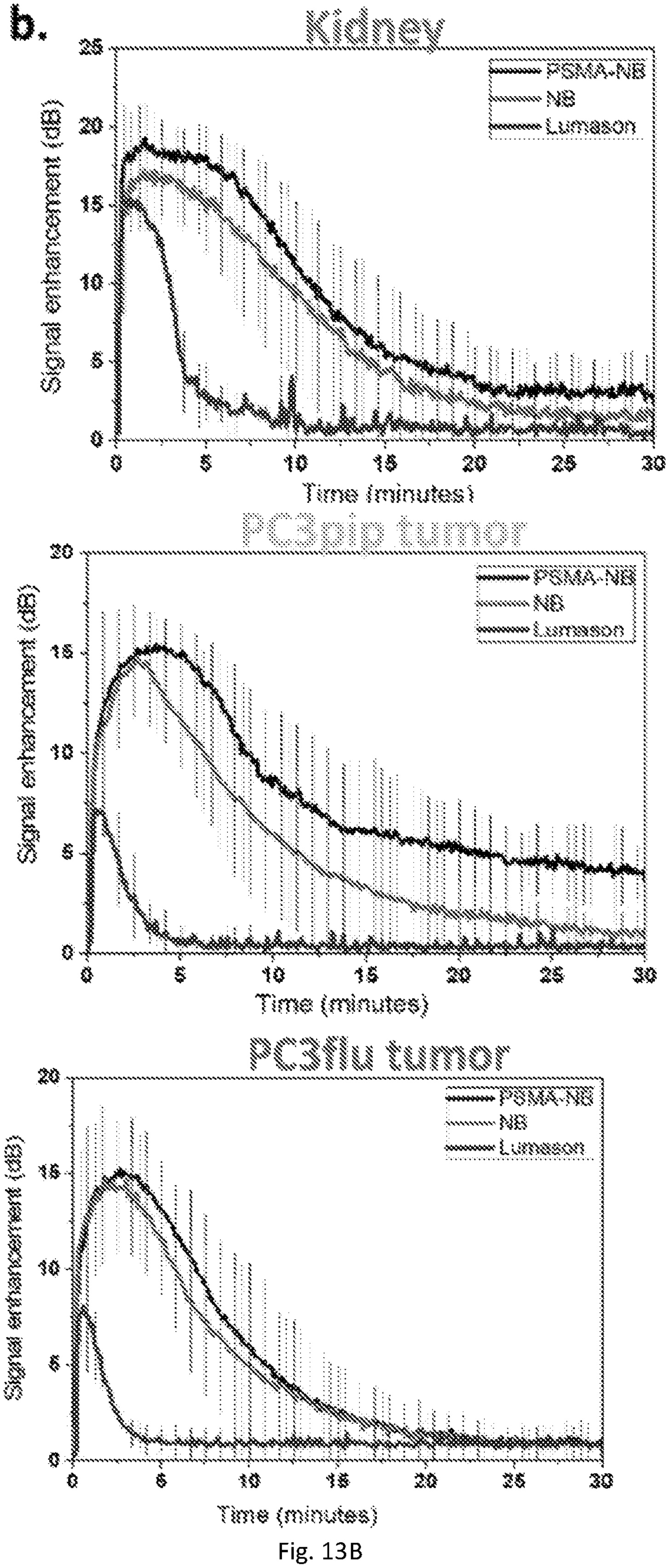

The nanobubbles can be used as contrast agents to enhance ultrasound images of the vascular capillary bed as their smaller size and higher number density enables them to reach smaller blood vessels, resulting in superb image quality without significant signal attenuation (which is a problem with larger microbubbles at higher concentrations). Nanobubbles can extravasate beyond hyperpermeable vasculature into the tissue parenchyma in tumors or other pathologies exemplified by inflammation and hallmarked by vascular hyperpermeability (such as type 1 diabetes). FIG. 11, FIG. 12 and FIG. 13 show data supporting this in colorectal and prostate cancers.

Nanobubbles can also be used to carry drug at a much higher level and with extended in vivo circulation time and can be destroyed with ultrasound on demand to increase drug delivery efficiency in tumors. Nanobubble shell can have cargo included for drug delivery. Cargo can be small molecule drug, antibody, peptide or DNA, RNA, siRNA etc. In FIG. 15 we show nanobubbles loaded with the anticancer drug Doxorubicin, and their stability in vitro.

Figure 14:
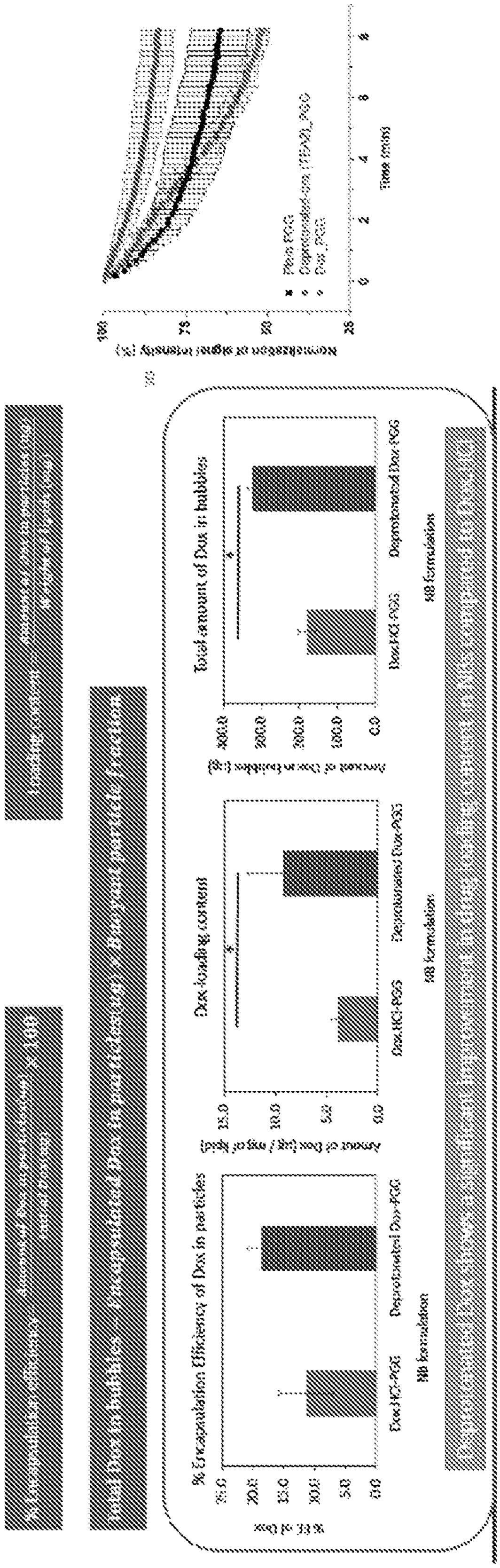
FIG. 14 illustrates deprotonated Doxorubicin loaded into ultrastable nanobubbles increases the loading capacity and stability of the ultrastable nanobubbles.
Figure 15A:
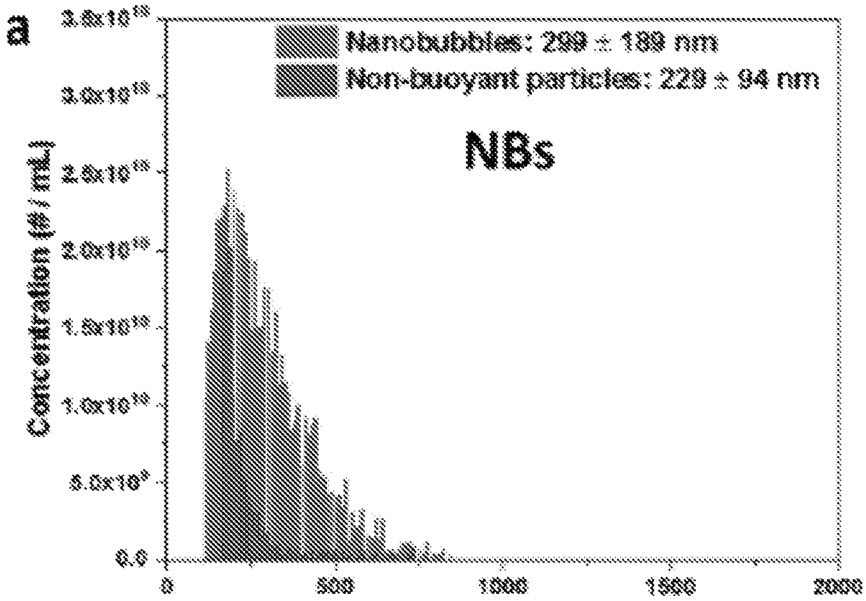
FIGS. 15(A-D) illustrate nanobubbles and microbubbles were characterized using resonant mass measurement (Archimedes) (A-B), which gives the size and concentration for both bubbles and non-buoyant particles present in the sample. Optical microscopy images (63× zoom) of (C) nanobubbles (NBs) and (D) microbubbles (MBs). Average size and size distribution were quantified using ImageJ software.
Figure 15B:
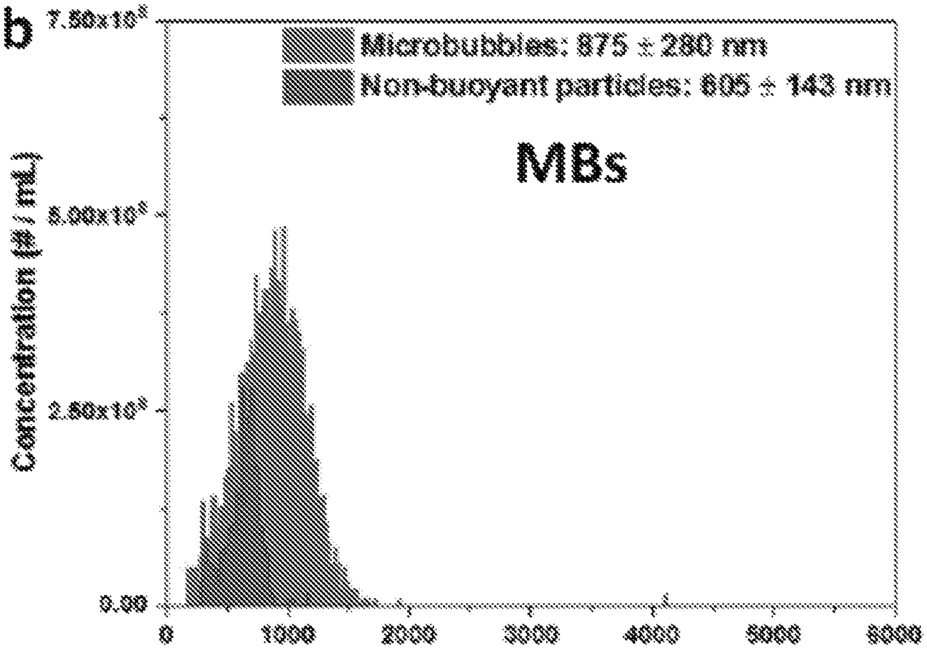
Figure 15C:
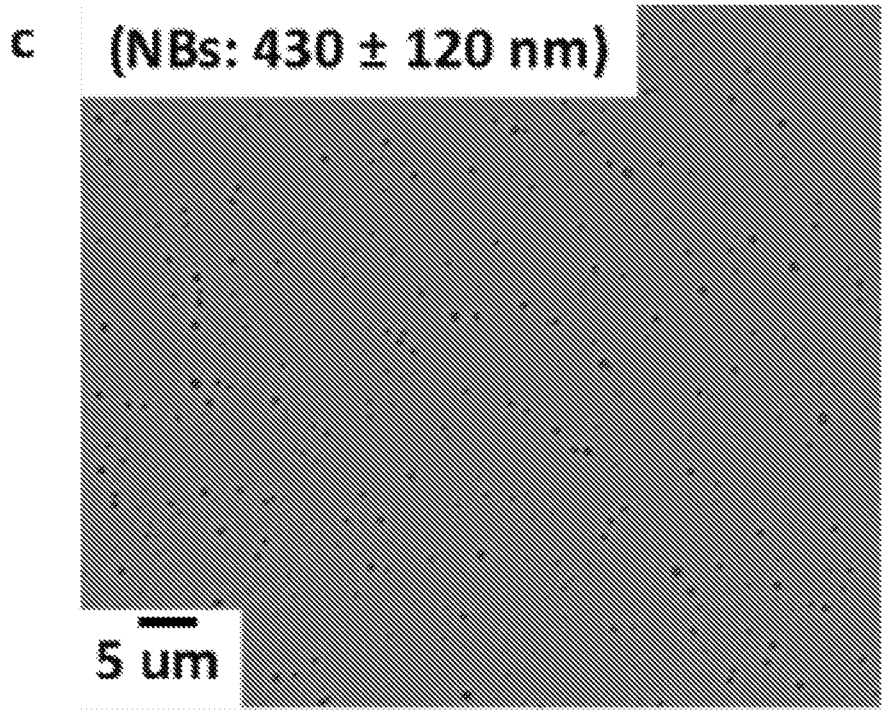
Figure 15D:
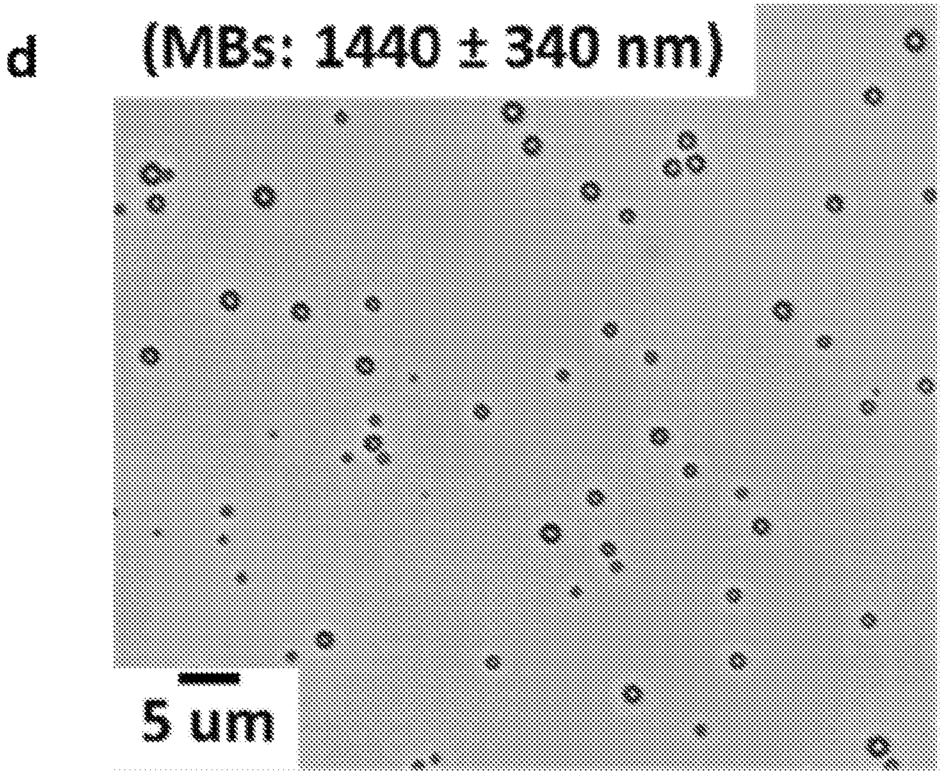
Figure 16A:
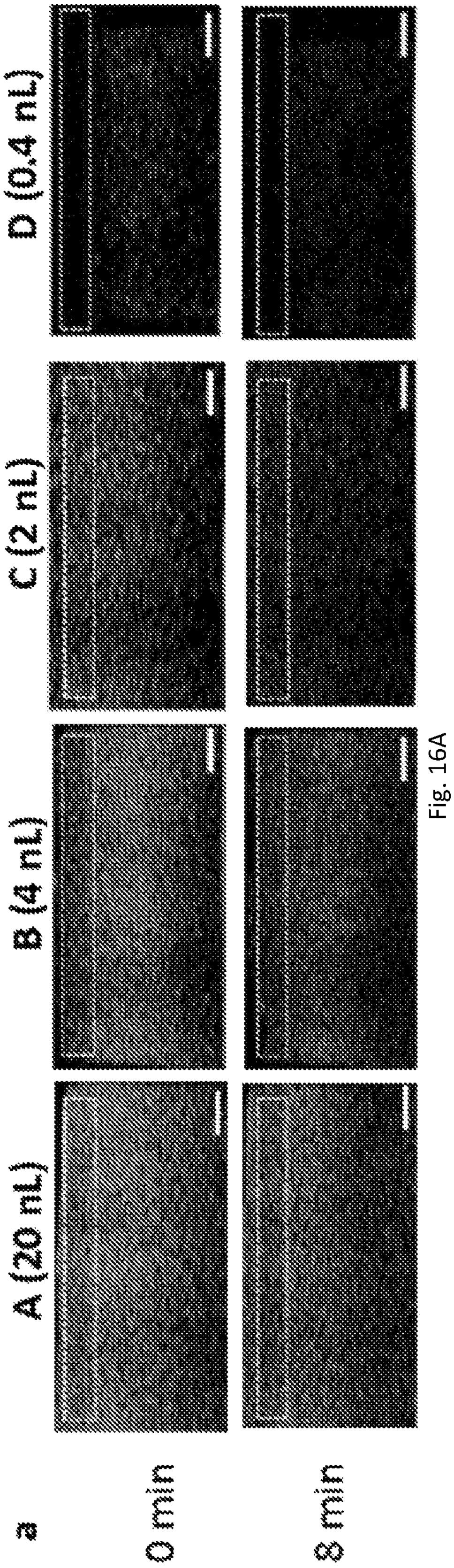
FIGS. 16(A-D) illustrate (A and B) In vitro contrast harmonic images (harmonic frequency, 12.0 MHz; MI, 0.10; imaging frame rate, 1 frame/s) at different gas volumes of PG-Gly-NBs and PG-Gly-MBs, respectively. Scale bar is 0.5 cm. The yellow box indicates the region of interest (ROI) where US signal was quantified for each gas volume. Corresponding ultrasound signal time intensity curves for NBs (c) and MBs (d) at different gas volume.
Figure 16B:
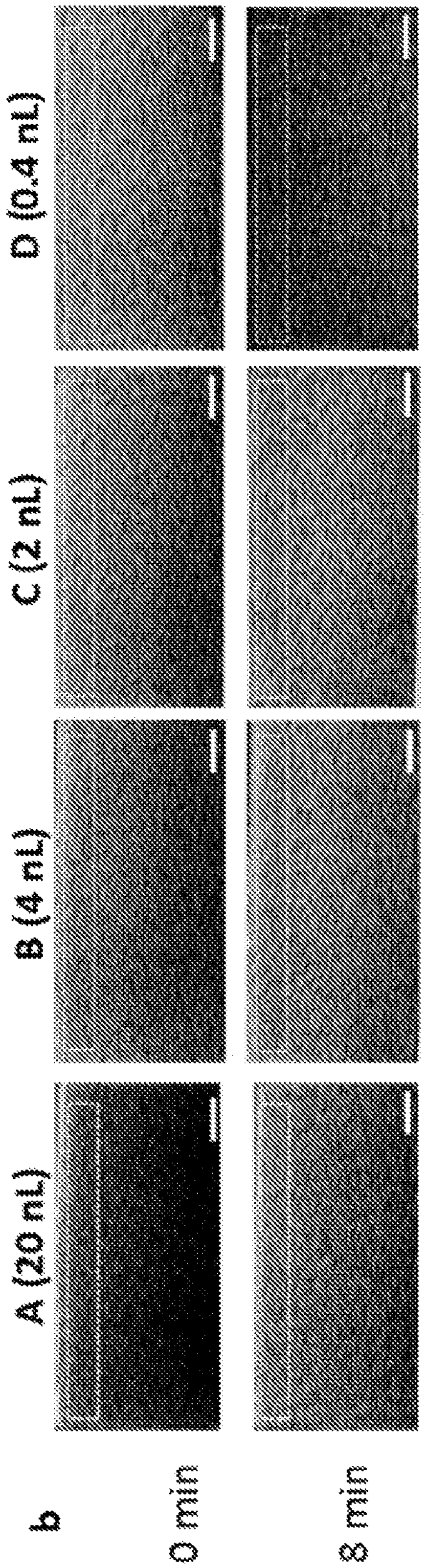
Figure 16C:
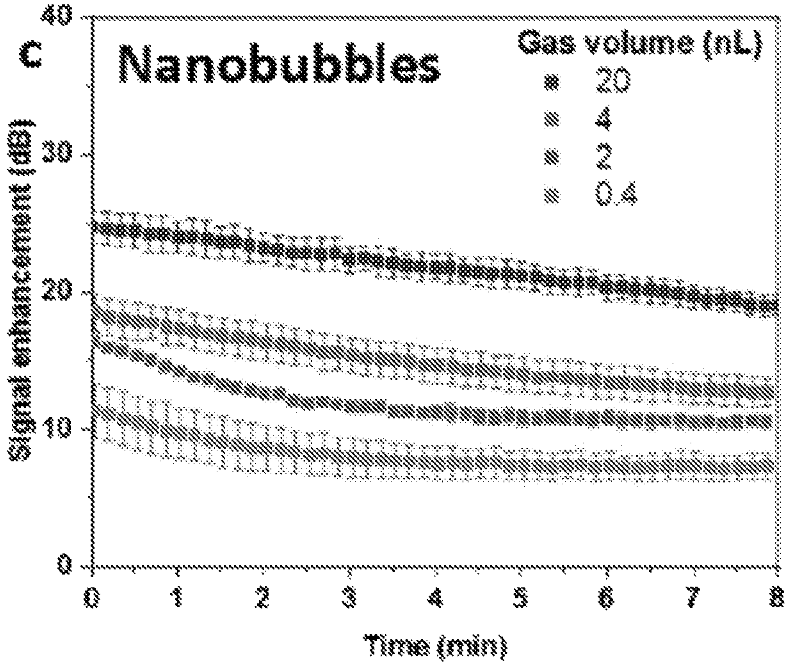
Figure 16D:
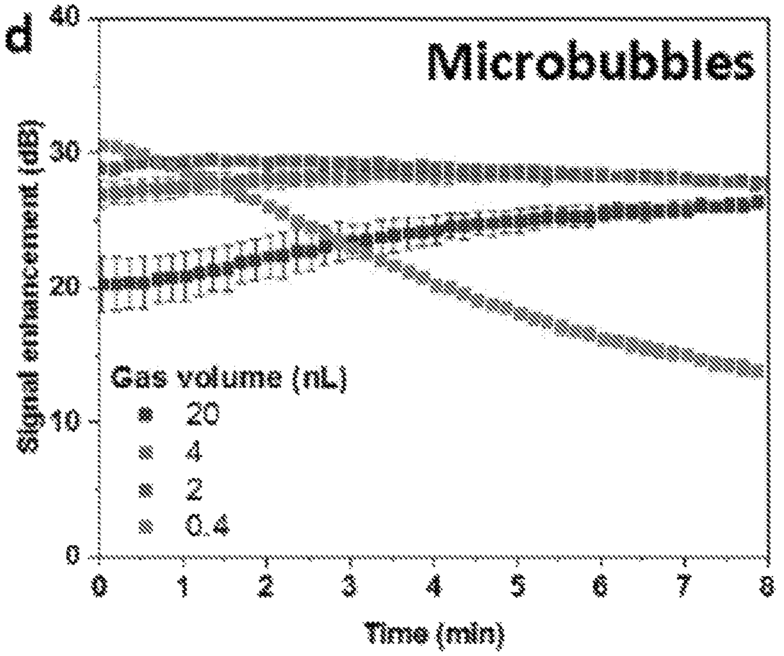
Figure 17A:
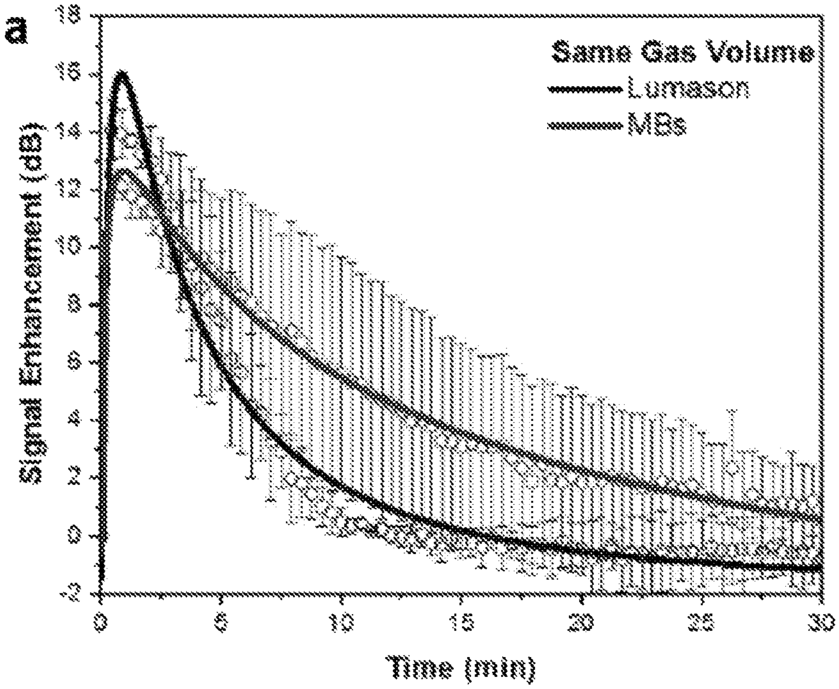
FIGS. 17(A-D) illustrate in vivo ultrasound (US) measurements (harmonic frequency, 12.0 MHz; MI, 0.10; imaging frame rate, 12 frames/min) using healthy mice at the same gas volume concentration ($6.45\times10^{16}$ $nm^3$/mL) show higher signal enhancement over time for MBs compared to Lumason (A) with both curves following a lognormal function characterized by a sudden sharp increase in signal and a quick onset of gradually decaying signal (B). Corresponding B-mode and contrast harmonic images of mice kidney are shown in (C) and (D) for Lumason and MBs, respectively. A total of three replicates were performed for each condition. Scale bar is 0.5 cm.
Figure 17B:
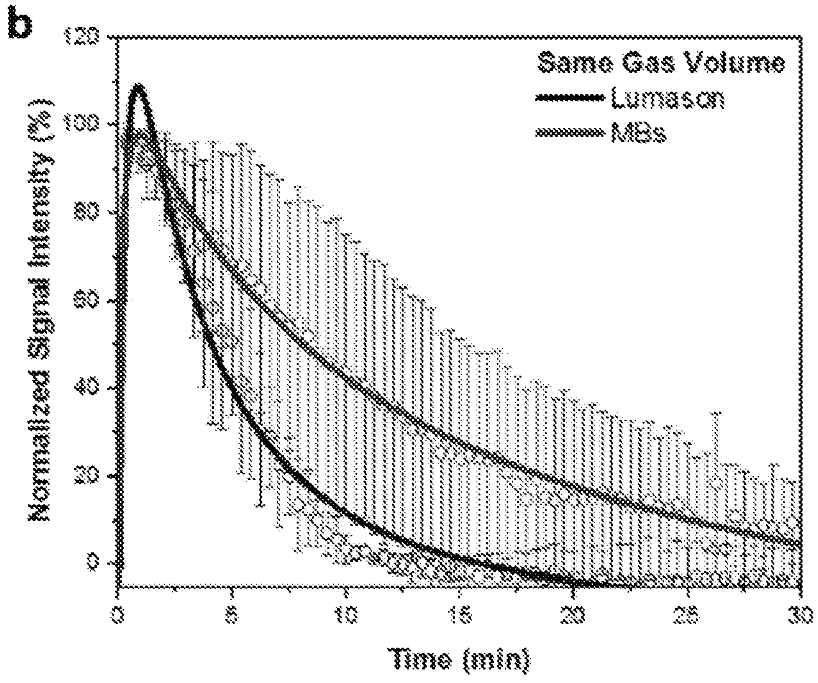
Figure 17C:
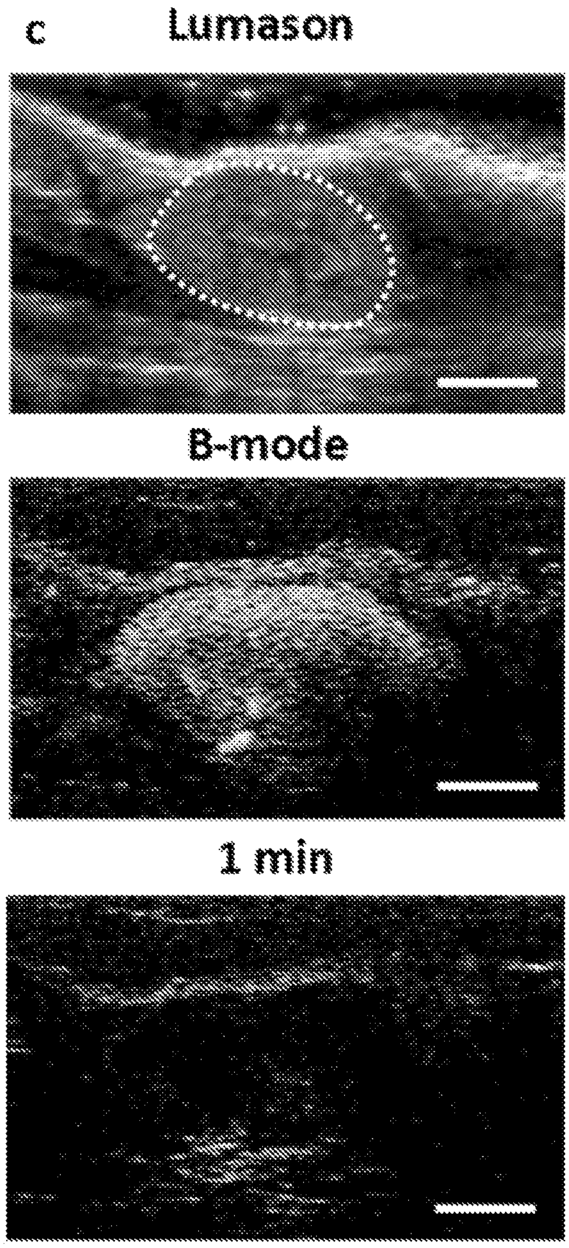
Figure 17D:
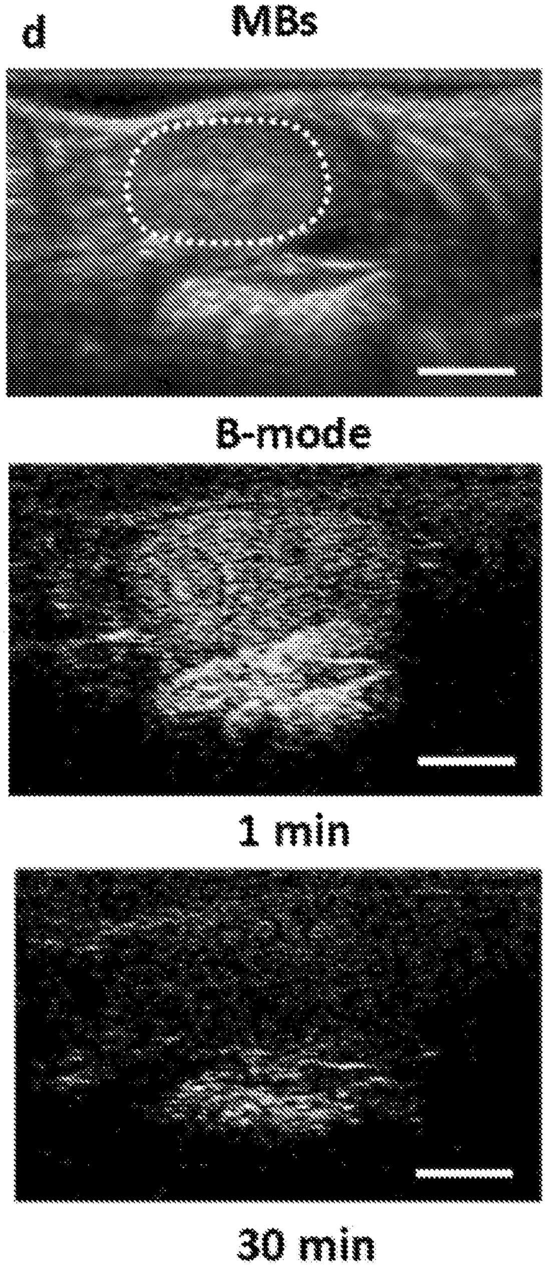

The formulation can be separated into microbubbles and nanobubbles and both sizes are quite stable, and significantly more stable than currently available commercial microbubbles (FIG. 14). Both nanobubbles and microbubbles have a yield which is 3-5 orders of magnitude higher than clinically available bubbles (10e11 for nanobubbles and 10e10 for microbubbles). FIG. 15-16.

FIGS. 17(A-D) illustrate in vivo ultrasound (US) measurements (harmonic frequency, 12.0 MHz; MI, 0.10; imaging frame rate, 12 frames/min) using healthy mice at the same gas volume concentration ($6.45 \times 10^{16}$ $nm^3$/mL) show higher signal enhancement over time for MBs compared to Lumason (A) with both curves following a log normal function characterized by a sudden sharp increase in signal and a quick onset of gradually decaying signal (B). Corresponding B-mode and contrast harmonic images of mice kidney are shown in (C) and (D) for Lumason and MBs, respectively. A total of three replicates were performed for each condition. Scale bar is 0.5 cm.

Figure 18A:
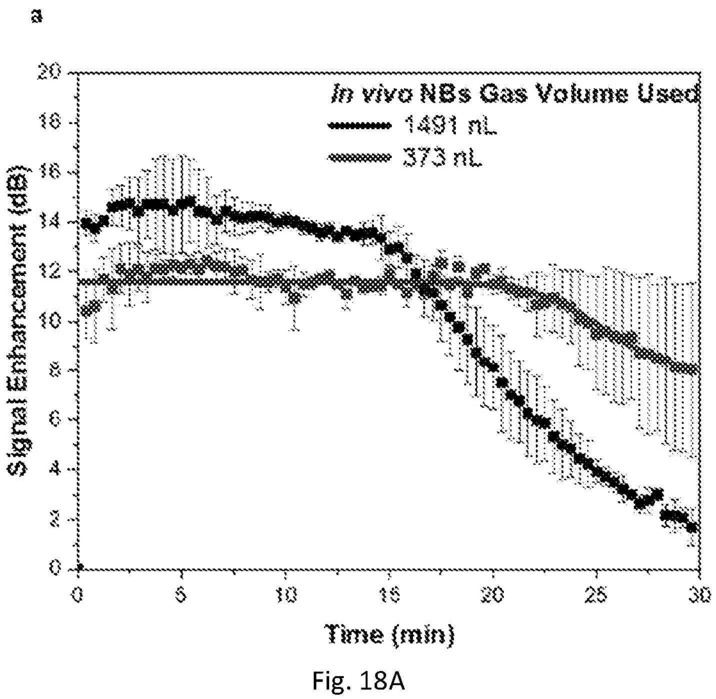
FIGS. 18(A-C) illustrate in vivo ultrasound (US) measurements (harmonic frequency, 12.0 MHz; MI, 0.10; imaging frame rate, 12 frame/min) using healthy mice at different gas volumes of nanobubbles. Both NB gas volume used follow a logistic curve function where the US signal maintained a steady state before the signal gradually decays. Corresponding B-mode and contrast harmonic images of mice kidney are shown in (B) and (C). A total of three replicates were performed for each condition. Scale bar is 0.5 cm.
Figure 18B:
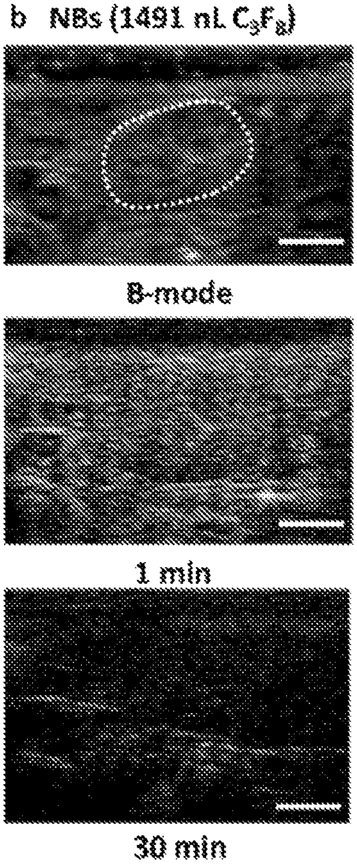
Figure 18C:
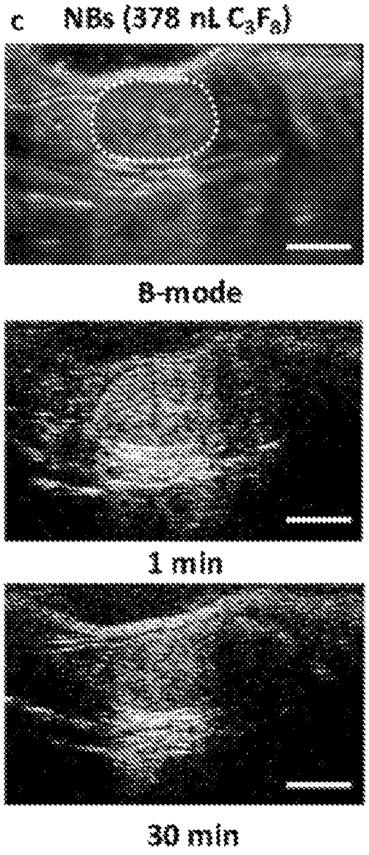

FIGS. 18(A-C) illustrate in vivo ultrasound (US) measurements (harmonic frequency, 12.0 MHz; MI, 0.10; imaging frame rate, 12 frame/min) using healthy mice at different gas volumes of nanobubbles. Both NB gas volume used follow a logistic curve function where the US signal maintained a steady state before the signal gradually decays. Corresponding B-mode and contrast harmonic images of mice kidney are shown in (B) and (C). A total of three replicates were performed for each condition. Scale bar is 0.5 cm.

Figure 19A:
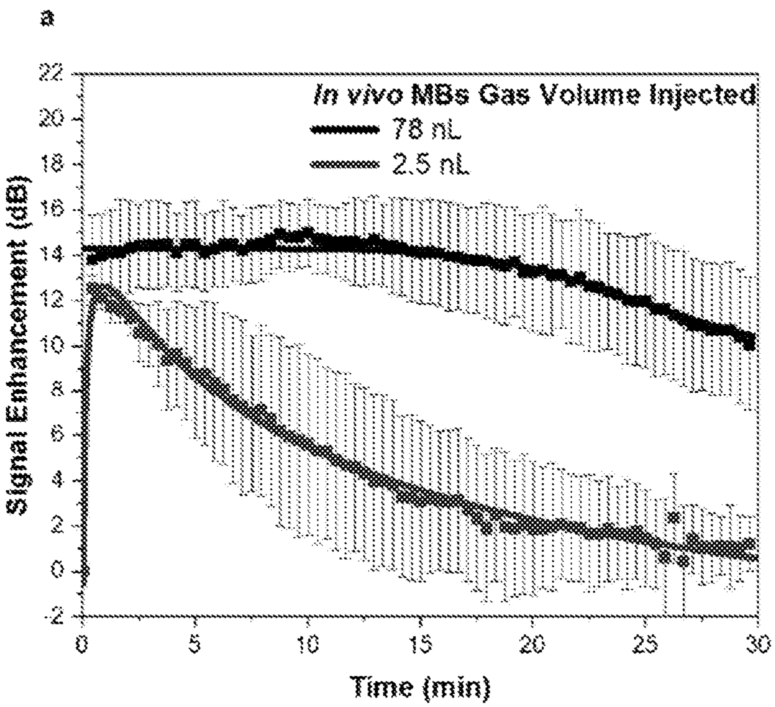
FIGS. 19(A-C) illustrate in vivo ultrasound (US) measurements (harmonic frequency, 12.0 MHz; MI, 0.10; imaging frame rate, 12 frames/min) using healthy mice at different gas volume for MBs. (a) Higher signal enhancement over time for MBs with a higher gas volume, and the signal decay follows a logistic function. On the other hand, at low gas volume, the curve follows a log normal function characterized by a sudden sharp increase in signal and a quick onset of gradually decaying signal. (B and C) Corresponding B-mode and contrast harmonic images of mice kidney are shown at different gas volume, 78 nL and 2.5 nL, respectively. A total of three replicates were performed for each condition. Scale bar is 0.5 cm.
Figure 19B:
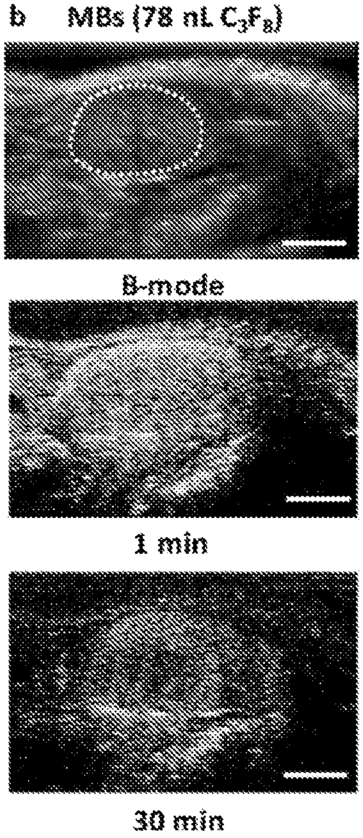
Figure 19C:
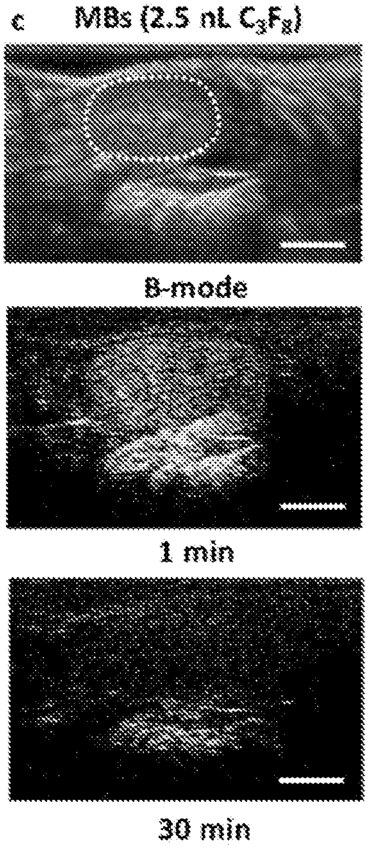

FIGS. 19(A-C) illustrate in vivo ultrasound (US) measurements (harmonic frequency, 12.0 MHz; MI, 0.10; imaging frame rate, 12 frames/min) using healthy mice at different gas volume for MBs. (a) Higher signal enhancement over time for MBs with a higher gas volume, and the signal decay follows a logistic function. On the other hand, at low gas volume, the curve follows a log normal function characterized by a sudden sharp increase in signal and a quick onset of gradually decaying signal. (B and C) Corresponding B-mode and contrast harmonic images of mice kidney are shown at different gas volume, 78 nL and 2.5 nL, respectively. A total of three replicates were performed for each condition. Scale bar is 0.5 cm.

Figure 20:
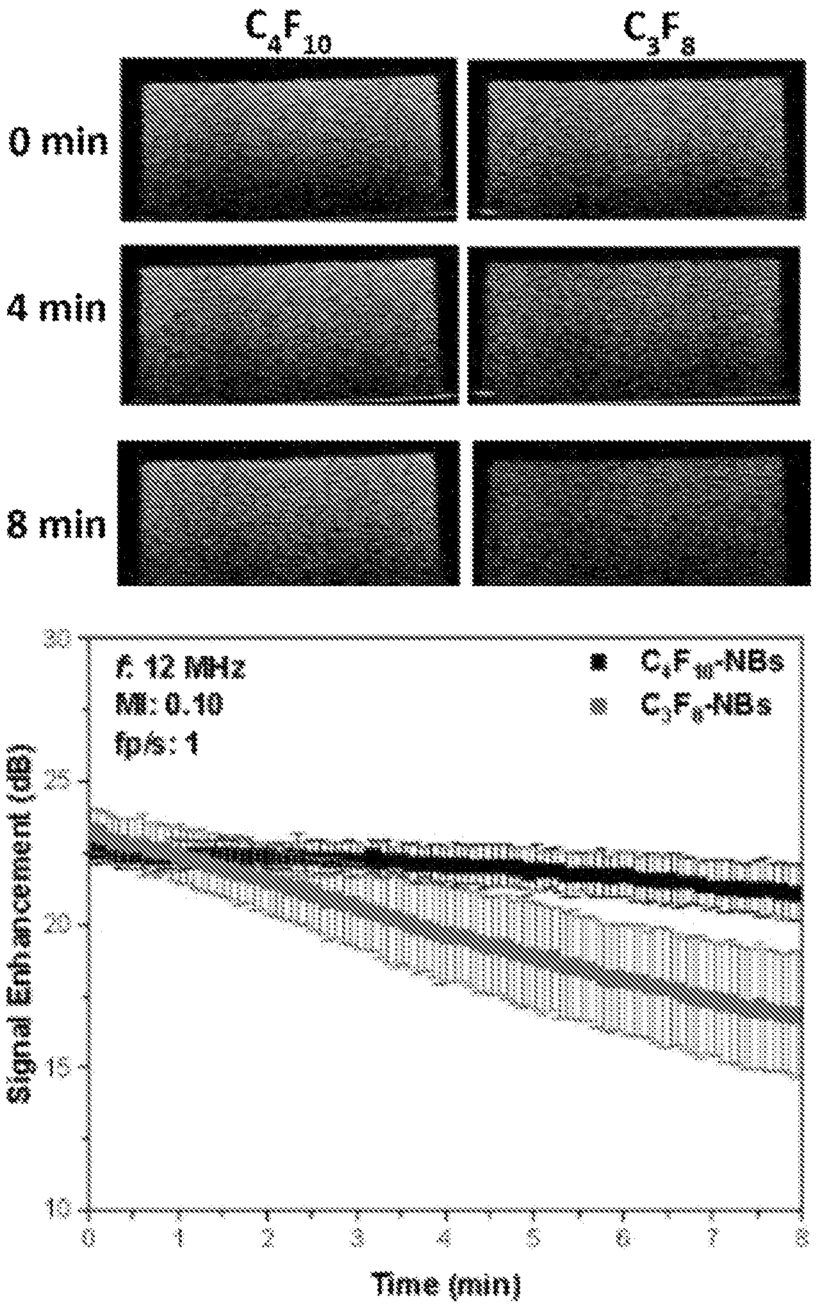
FIG. 20 illustrates ultrasound images and rates of signal decay for nanobubbles filled with $C_4F_{10}$ versus $C_3F_8$. The $C_4F_{10}$ nanobubbles appear to be significantly more stable, exhibiting 0 signal loss in the 8 minute experiments, compared to a 30% signal loss to the original $C_3F_8$ formulation.

We can fill the bubble core with other perfluorocarbon in addition to $C_3F_8$ such as $C4F_{10}$ or other fluorinated gas such as $SF_6$. FIG. 20 shows bubble stability with $C_4F_{10}$.

Figure 21:
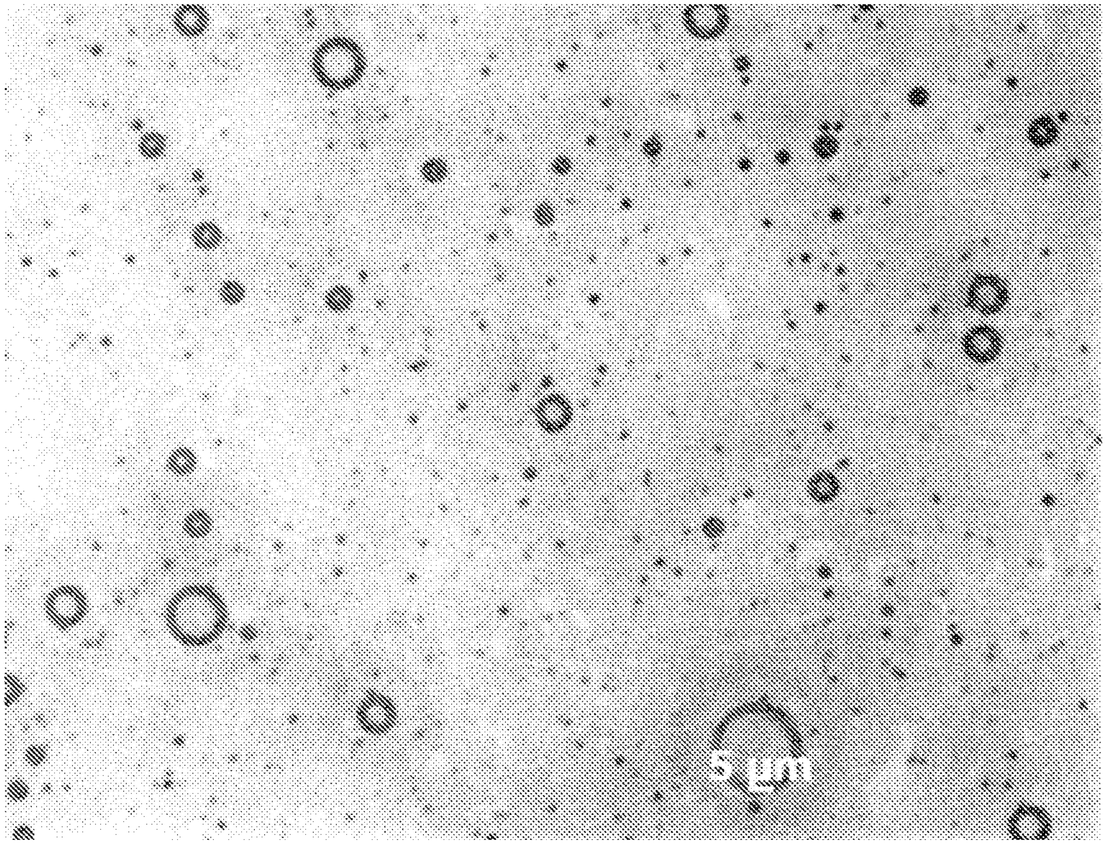
FIG. 21 illustrates ultrastable bubbles labeled with Texas Red. The fluorescence image was overlaid on brightfield image to show the dye is loaded into the bubble shell.

Nanobubble shell can be made fluorescent for dual-mode optical and ultrasound imaging. In FIG. 21 we show fluorescent bubbles labeled with Texas Red.

Main differences in formulation compared to the closest commercial microbubble, Definity® are listed in the tables below. The primary differences are highlighted.

TABLE 2

| Components | Molecular Weight | Mass per 1 mL solution (mg) | mmoles | Ration |
|---|---|---|---|---|
| PG-22 | | | | |
| C22 | 902.358 | 6.1 | 6.76E−03 | 18.97 |
| DPPA | 670.873 | 1 | 1.49E−03 | 4.18 |
| DPPE | 691.959 | 2 | 2.89E−03 | 8.11 |
| DSPE-Mpeg 2k | 2805.497 | 1 | 3.56E−04 | 1.00 |
| Glycerol | 92.09 | 126 | 1.37E+00 | 3838.56 |
| Propylene Glycol | 76.01 | 104 | 1.37E+00 | 3838.60 |
| Water | 18 | 800 | 4.44E+01 | 124688.76 |
| Definity (commercially available) | | | | |
| C16 | 734.039 | 0.401 | 5.46E−04 | 10.32 |
| DPPA | 970.873 | 0.045 | 6.71E−05 | 1.27 |
| DPPE | 691.959 | 0 | 0.00E+00 | 0.00 |
| DSPE-Mpeg 2k | 5744.965 | 0.304 | 5.29E−05 | 1.00 |
| Glycerol | 92.09 | 126 | 1.37E+00 | 25856.63 |
| Propylene Glycol | 76.01 | 104 | 1.37+00 | 25856.90 |
| Water | 18 | 800 | 4.44E+01 | 839907.16 |

To summarize, our PG/Gly bubbles (on the table referred to as PG-C22) use C22 (DBPC) instead of C16 (DPPC), they include DPPE, the use DSPE-PEG2000 instead of DSPE-PEG5000 and use much higher lipid concentration in PBS.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, the following is claimed:

1. A composition comprising:

a plurality of stabilized nanobubbles, each nanobubble having a lipid membrane that defines at least one internal void, which includes at least one gas, the membrane of each nanobubble consisting essentially of a plurality of lipids, which are a mixture of dibehenoylglycerophosphocoline (DBPC), dipalmitoylphosphatidic acid (DPPA), dipalmitoylphosphatidylethanolamine (DPPE), and PEG functionalized distearoylphosphatidylethanolamine (DSPE); propylene glycol that is incorporated between lipids of the membrane; and glycerol that is incorporated on an outer surface of the membrane, wherein the nanobubbles have an average diameter of about 30 nm to about 600 nm, the propylene glycol is the only cosurfactant or surfactant incorporated in the membrane besides the plurality of lipids, and the stabilized nanobubbles have a lipid concentration of at least 5 mg/ml.

2. The composition of claim 1, wherein the mixture includes at least about 50% by weight of dibehenoylglycerophosphocoline (DBPC) and less than about 50% by weight of dipalmitoylphosphatidylethanolamine (DPPE), PEG functionalized distearoylphosphatidylethanolamine (DSPE), and dipalmitoylphosphatidic acid (DPPA).

3. The composition of claim 1, wherein the mixture of dibehenoylglycerophosphocoline (DBPC), dipalmitoylphosphatidic acid (DPPA), dipalmitoylphosphatidylethanolamine (DPPE), and distearoylphosphatidylethanolamine-N-methoxy-polyethylene glycol (DSPE-mPEG) are at a weight ratio of about 6:1:2:1.

4. The composition of claim 1, further comprising at least one targeting moiety that is linked to the membrane of each nanobubble.

5. The composition of claim 4, the targeting moiety being selected from the group consisting of polypeptides, polynucleotides, small molecules, elemental compounds, antibodies, and antibody fragments.

6. The composition of claim 1, further comprising at least one therapeutic agent that is contained within the membrane or conjugated to the membrane of each nanobubble.

7. The composition of claim 6, the therapeutic agent further comprising at least one chemotherapeutic agent, anti-proliferative agent, biocidal agent, biostatic agent, or anti-microbial agent.

8. A method for imaging a region of interest (ROI) in a subject, the method comprising the steps of:

administering to the subject a plurality of stabilized nanobubbles of claim 1; and generating at least one image of the ROI by nonlinear ultrasound imaging the nanobubbles in the ROI.

9. The method of claim 8, the step of administering the composition to the subject further comprising the step of generating at least one baseline image of the ROI prior to administering the composition.

10. A method of assessing vascular permeability of vasculature of a subject in need thereof, the method comprising:

administering to the subject a plurality of stabilized nanobubbles of claim 1; and generating at least one intravascular and/or extravascular ultrasound image to determine extravasation of the nanobubbles and permeability of the vasculature.

11. The composition of claim 1, wherein the membrane consists of a plurality of lipids, which are a mixture of dibehenoylglycerophosphocoline (DBPC), dipalmitoylphosphatidic acid (DPPA), dipalmitoylphosphatidylethanolamine (DPPE), and PEG functionalized distearoylphosphatidylethanolamine (DSPE); propylene glycol that is incorporated between lipids of the membrane; and glycerol that is incorporated on an outer surface of the membrane.

* * * * *